(12) United States Patent
Chin et al.

(10) Patent No.: US 8,641,733 B2
(45) Date of Patent: Feb. 4, 2014

(54) SYSTEM AND METHOD FOR FACET FIXATION

(75) Inventors: Kingsley R. Chin, West Palm Beach, FL (US); Christopher A. Chang, Beverly, MA (US)

(73) Assignee: Spinefrontier Inc, Beverly, MA (US)

( * ) Notice: Subject to any disclaimer, the term of this patent is extended or adjusted under 35 U.S.C. 154(b) by 106 days.

(21) Appl. No.: 13/453,044

(22) Filed: Apr. 23, 2012

(65) Prior Publication Data
US 2012/0209327 A1 Aug. 16, 2012

Related U.S. Application Data

(63) Continuation-in-part of application No. 11/779,526, filed on Jul. 18, 2007, now Pat. No. 8,002,799, and a continuation of application No. 12/543,656, filed on Aug. 19, 2009, now Pat. No. 8,231,660, and a continuation of application No. 11/955,621, filed on Dec. 13, 2007.

(51) Int. Cl.
*A61B 17/56* (2006.01)

(52) U.S. Cl.
USPC ......................................... 606/246

(58) Field of Classification Search
USPC ......... 606/246–248, 264, 268, 279, 280, 284, 606/286, 287, 289, 291, 295, 297, 301, 304, 606/308, 323, 104; 623/13.14
See application file for complete search history.

(56) References Cited

U.S. PATENT DOCUMENTS 2,570,465 A * 10/1951 Lundholm ...................... 606/65
4,988,351 A * 1/1991 Paulos et al. .................. 606/232

* cited by examiner

*Primary Examiner* — Pedro Philogene
*Assistant Examiner* — David Comstock
(74) *Attorney, Agent, or Firm* — AKC Patents LLC; Aliki K. Collins

(57) ABSTRACT

A spinal fixation element includes a screw and a washer. The screw comprises an elongated body of a first diameter and the body includes a threaded portion at a distal end and a semispherical head of a second diameter at a proximal end. The second diameter is larger than the first diameter. The washer comprises a semispherical through opening of a third diameter at the top, of a fourth diameter in the middle and of a fifth diameter at the bottom. The third diameter is slightly smaller than the second diameter, the fourth diameter is slightly larger than the second diameter and the fifth diameter is smaller than the second diameter. The washer surrounds the semispherical head, is non-removably attached to the semispherical head and is rotatable and positionable at an angle relative to the elongated body.

9 Claims, 30 Drawing Sheets

SYSTEM AND METHOD FOR FACET FIXATION

CROSS REFERENCE TO RELATED CO-PENDING APPLICATIONS

This application is a continuation in part of U.S. application Ser. No. 11/779,526 filed on Jul. 18, 2007 and entitled SYSTEM AND METHOD FOR FACET FIXATION the contents of which are expressly incorporated herein by reference.

This application is also a continuation of U.S. application Ser. No. 11/955,621 filed on Dec. 13, 2007 and entitled GUIDANCE SYSTEM, TOOLS, AND DEVICES FOR SPINAL FIXATION the contents of which are expressly incorporated herein by reference.

This application is also a continuation of U.S. application Ser. No. 12/543,656 filed on Aug. 19, 2009 and entitled SYSTEM AMD METHOD FOR FACET FIXATION the contents of which are expressly incorporated herein by reference.

FIELD OF THE INVENTION

The present invention relates to a system and a method for facet fixation, and more particularly to a facet fixation assembly including a polyaxial screw and a washer with protrusions.

BACKGROUND OF THE INVENTION

The human spine consists of individual vertebras that are connected to each other. Under normal circumstances the structures that make up the spine function to protect the neural structures and to allow us to stand erect, bear axial loads, and be flexible for bending and rotation. However, disorders of the spine occur when one or more of these spine structures are abnormal. In these pathologic circumstances, surgery may be tried to restore the spine to normal, achieve stability, protect the neural structures, or to relief the patient of discomfort. The goal of spine surgery for a multitude of spinal disorders especially those causing compression of the neural structures is often decompression of the neural elements and/or fusion of adjacent vertebral segments. Fusion works well because it stops pain due to movement at the facet joints or intervertebral discs, holds the spine in place after correcting deformity, and prevents instability and or deformity of the spine after spine procedures such as discectomies, laminectomies or corpectomies. Discectomy and fusion or corpectomy and fusion are most commonly performed in the cervical spine but there is increasing application in the thoracic and lumbar spine, as well.

Several spinal fixation systems exist for stabilizing the spine so that bony fusion is achieved. The majority of these fixation systems utilize fixation elements such as rods wires or plates that attach to screws threaded into the vertebral bodies, facets or the pedicles. Because the outer surface of the vertebral body is typically non-planar and the structure of the vertebras is relatively complex, it is important that the fixation elements (e.g., rods, plates, wires, staples and/or screws) are properly aligned when they are inserted into the vertebras. Improper alignment may result in improper or unstable placement of the fixation element and/or disengagement of the fixation element. However, achieving and maintaining accurate positioning and guidance of these fixation elements has proven to be quite difficult in practice. Such positioning difficulties are further complicated by the fact that the alignment angle for a fixation device through one vertebral body or pair of vertebral bodies will be unique to that individual due to individual differences in the spinal curvature and anatomies. Accordingly, there is a need for a method and a system for angular guiding and placing of spinal fixation elements.

SUMMARY OF THE INVENTION

In general, in one aspect, the invention features a spinal fixation element including a screw and a washer. The screw comprises an elongated body of a first diameter and the body includes a threaded portion at a distal end and a semispherical head of a second diameter at a proximal end. The second diameter is larger than the first diameter. The washer comprises a semispherical through opening of a third diameter at the top, of a fourth diameter in the middle and of a fifth diameter at the bottom. The third diameter is slightly smaller than the second diameter, the fourth diameter is slightly larger than the second diameter and the fifth diameter is smaller than the second diameter. The washer surrounds the semispherical head, is non-removably attached to the semispherical head and is rotatable and positionable at an angle relative to the semispherical head.

Implementations of this aspect of the invention may include one or more of the following features. The washer comprises protrusions extending from a bottom surface. The protrusions comprise one of spikes, teeth, serrations, grooves, or ridges. The protrusions are arranged around one or more circles concentric to the semispherical opening. The protrusions are spaced apart by gaps having alternating trigonal and rectangular shapes. The protrusions are arranged around an outer circle and an inner circle and the protrusions of the outer circle comprise teeth with rectangular cross-section and the protrusions of the inner circle comprise teeth with trigonal cross-section. The washer is non-removably attached to the semispherical head by swaging the top of the washer around the semispherical head. The angle varies between +30 degrees and −30 degrees relative to an axis passing through the center of the washer semispherical opening. The elongated body comprises a through opening extending from the proximal end to the distal end. The semispherical head comprises a flat top surface and a through opening being concentric with the through opening of the elongated body. The fixation element is made of stainless steel, titanium, plastic, bioabsorbable material, ceramic material, solid or porous material.

In general in another aspect the invention features a method for attaching a fixation element to a vertebral location including providing a fixation element. The fixation element comprises a screw and a washer. The screw comprises an elongated body of a first diameter and having a threaded portion at a distal end and a semispherical head of a second diameter at a proximal end. The second diameter is larger than the first diameter. The washer comprises a semispherical through opening of a third diameter at the top, of a fourth diameter in the middle and of a fifth diameter at the bottom. The third diameter is slightly smaller than the second diameter, the fourth diameter is slightly larger than the second diameter and the fifth diameter is slightly smaller than the second diameter. The washer surrounds the semispherical head, is non-removably attached to the semispherical head and is rotatable and positionable at an angle relative to the semispherical head. Next, inserting the screw into a vertebral location along a first direction, setting the washer at an angle relative to the first direction and securing the washer to the vertebral location by penetrating and grabbing an area around the vertebral location with the teeth and then screwing the threaded portion of the screw into the vertebral location.

BRIEF DESCRIPTION OF THE DRAWINGS

Referring to the figures, wherein like numerals represent like parts throughout the several views.

DETAILED DESCRIPTION OF THE INVENTION

Figure 1:
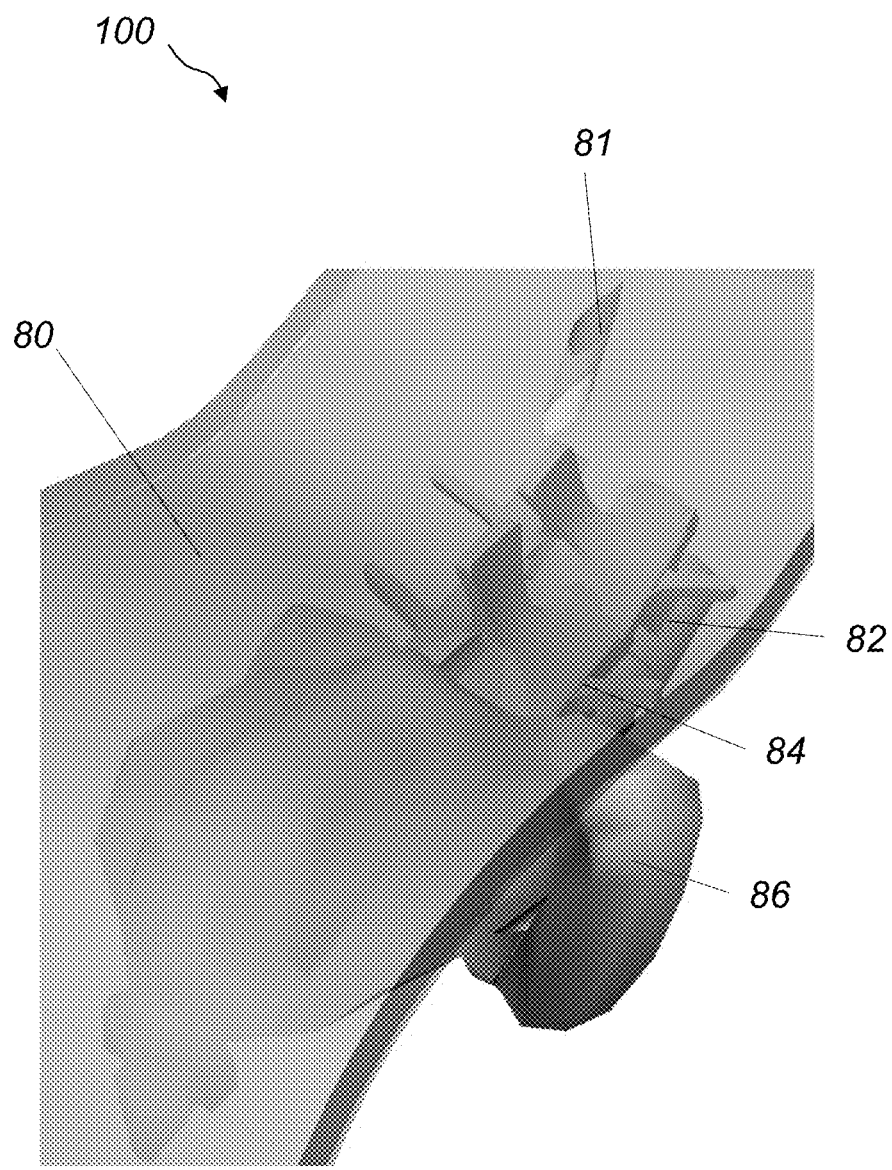
FIG. 1 is a schematic posterior view of a patient's lower back.
Figure 2:
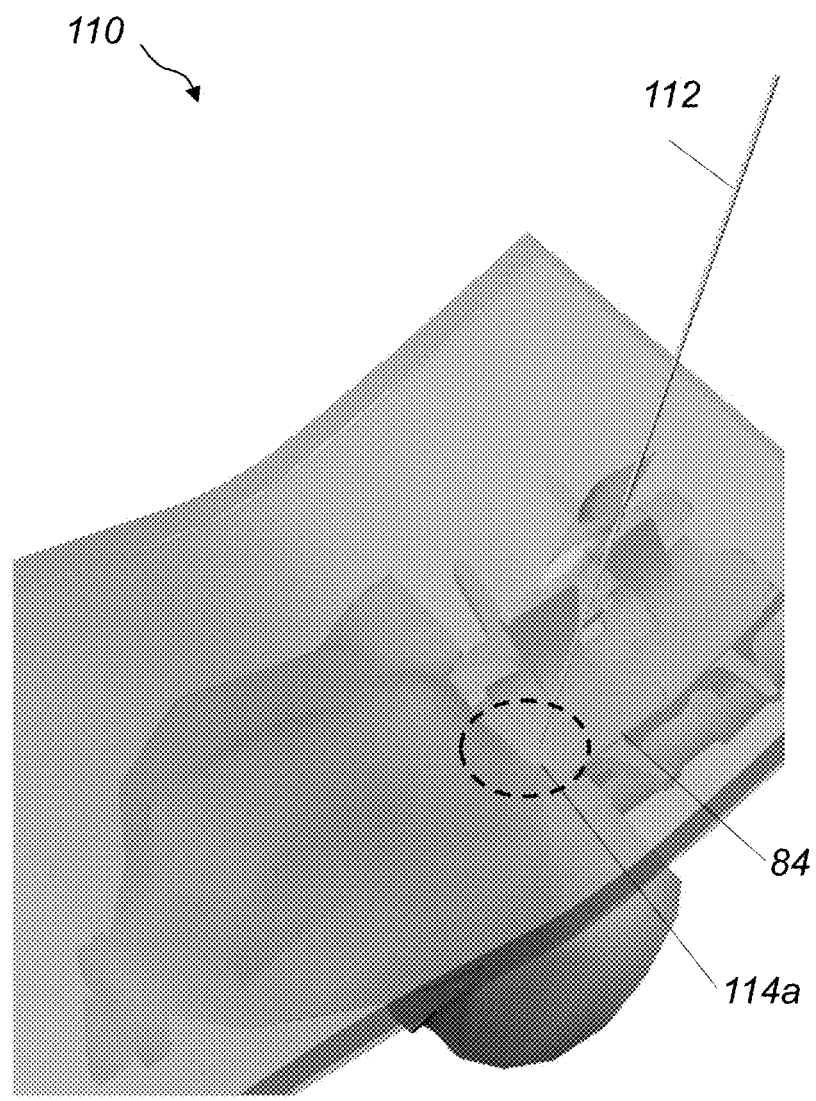
FIG. 2 depicts inserting a first guide wire into the patient's back of FIG. 1.
Figure 3:
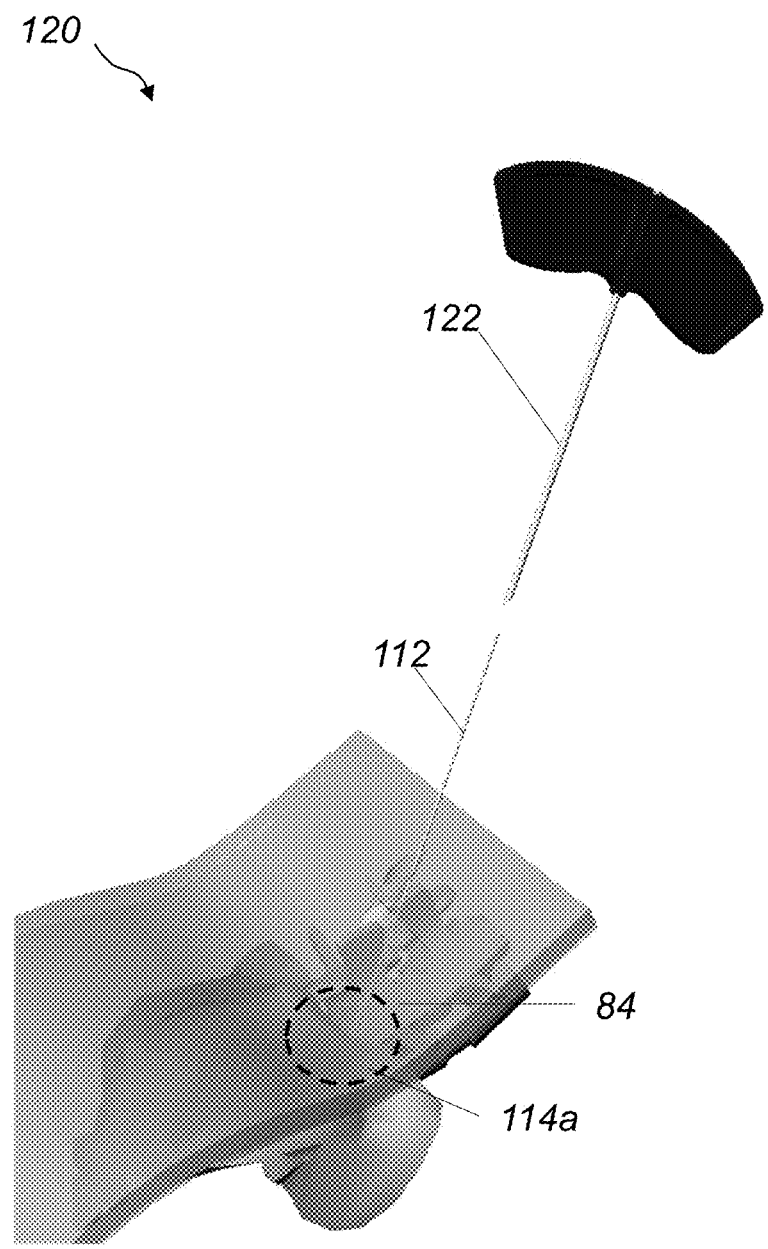
FIG. 3 depicts inserting a bone needle over the first guide wire of FIG. 2.
Figure 4:
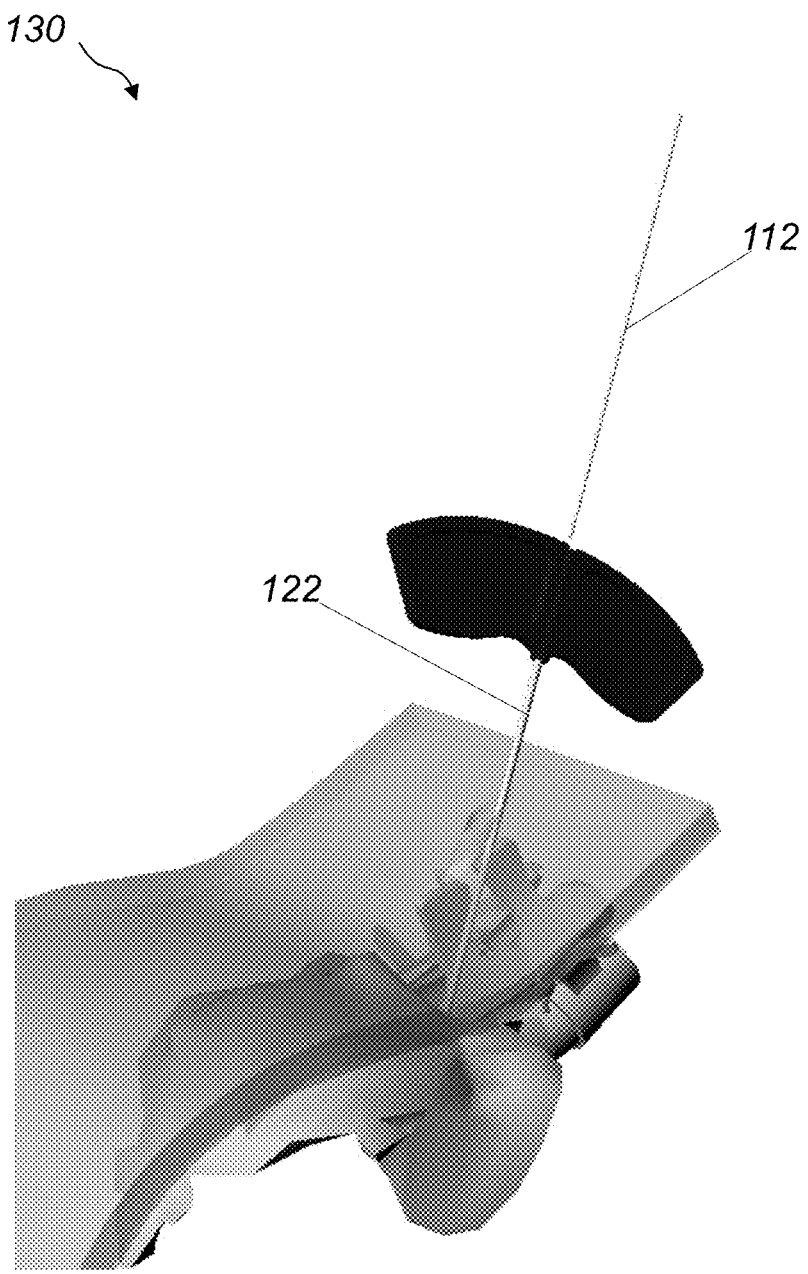
FIG. 4 depicts tapping the bone with the bone needle of FIG. 3.
Figure 5:
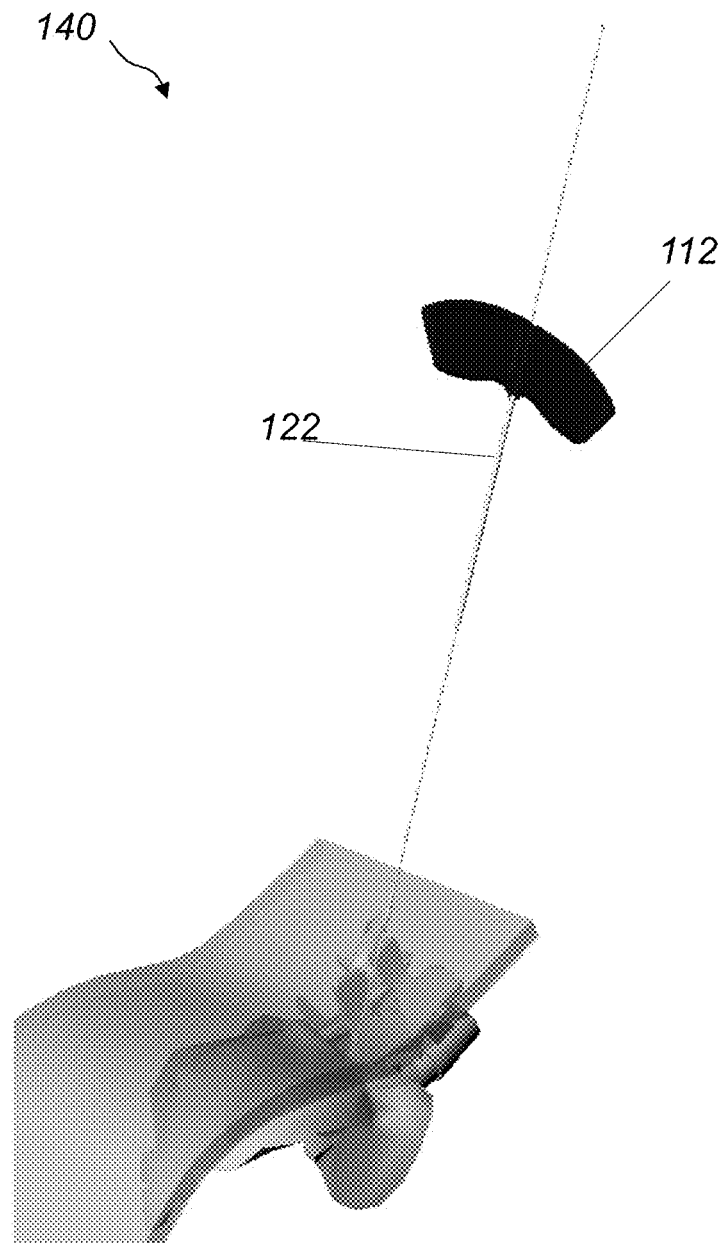
FIG. 5 depicts removing the bone needle.
Figure 6:
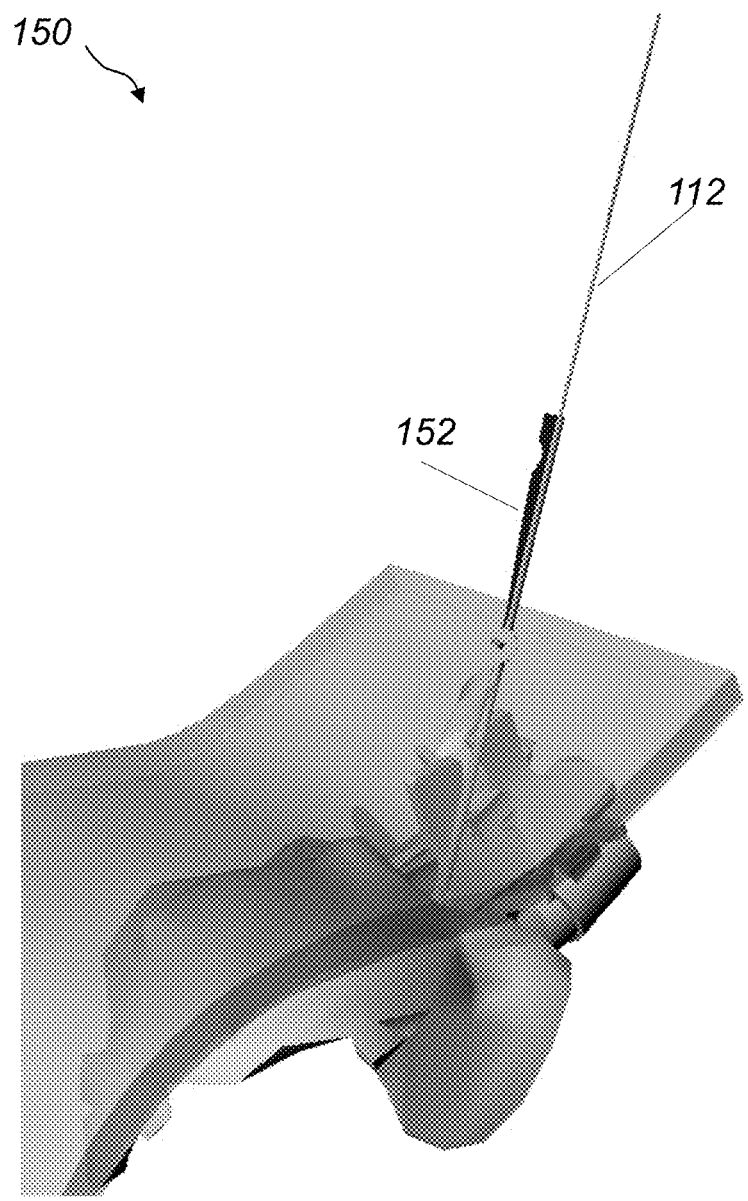
FIG. 6 depicts inserting the first guide member over the first guide wire of FIG. 5.
Figure 7:
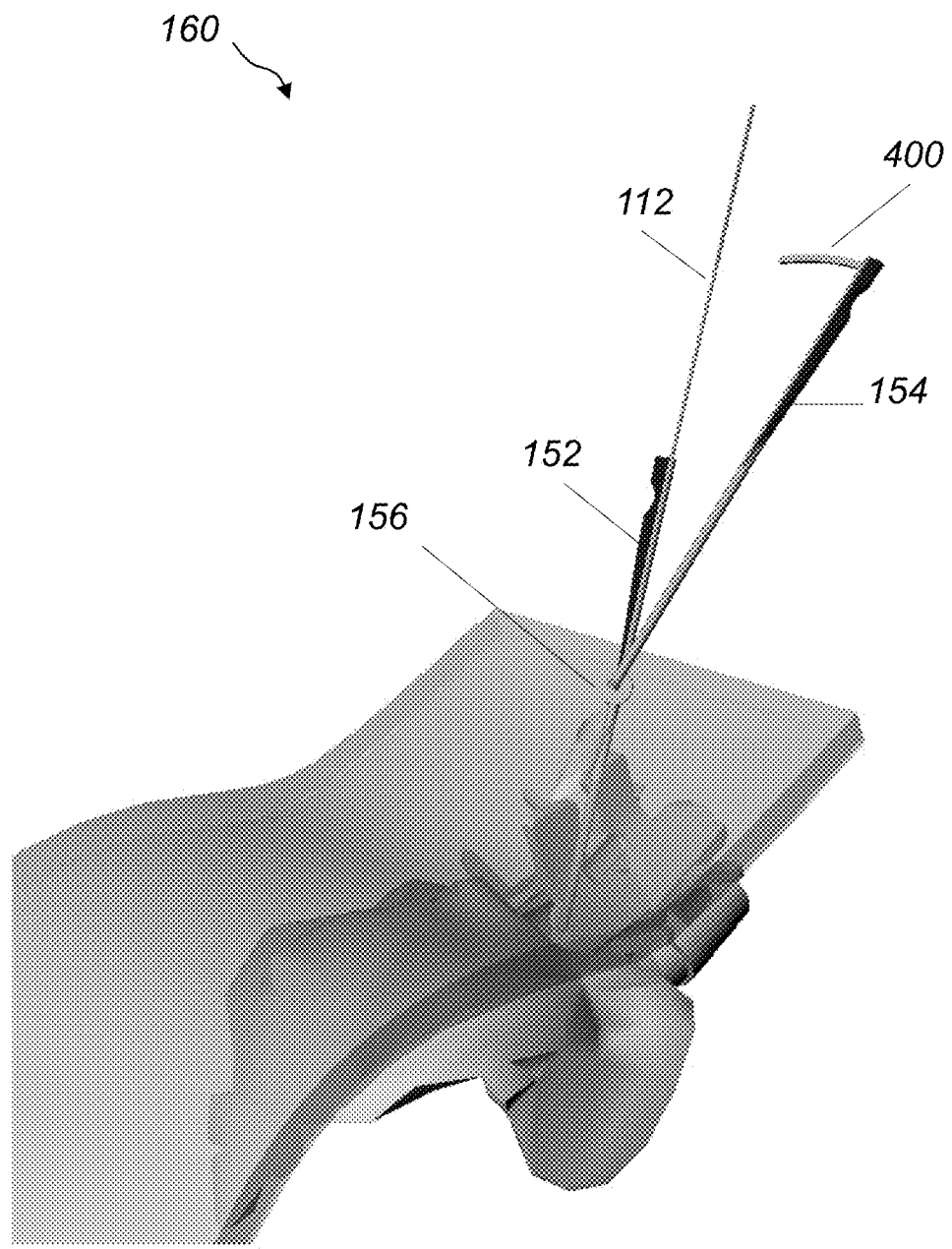
FIG. 7 depicts connecting the second guide member to the first guide member of FIG. 6.
Figure 8:
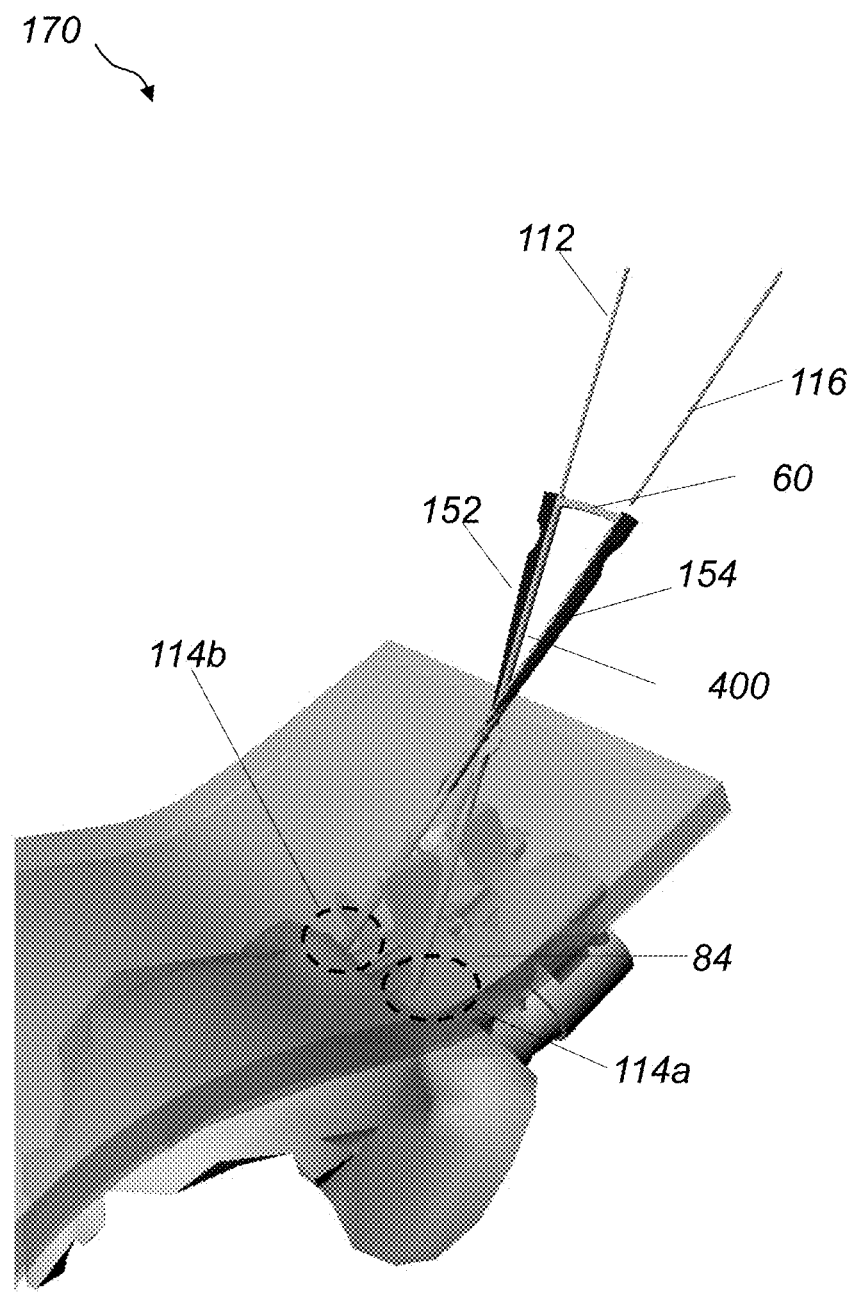
FIG. 8 depicts setting the angle between the first and second guide members and inserting a second guide wire through the second guide member into the patient's back.
Figure 9:
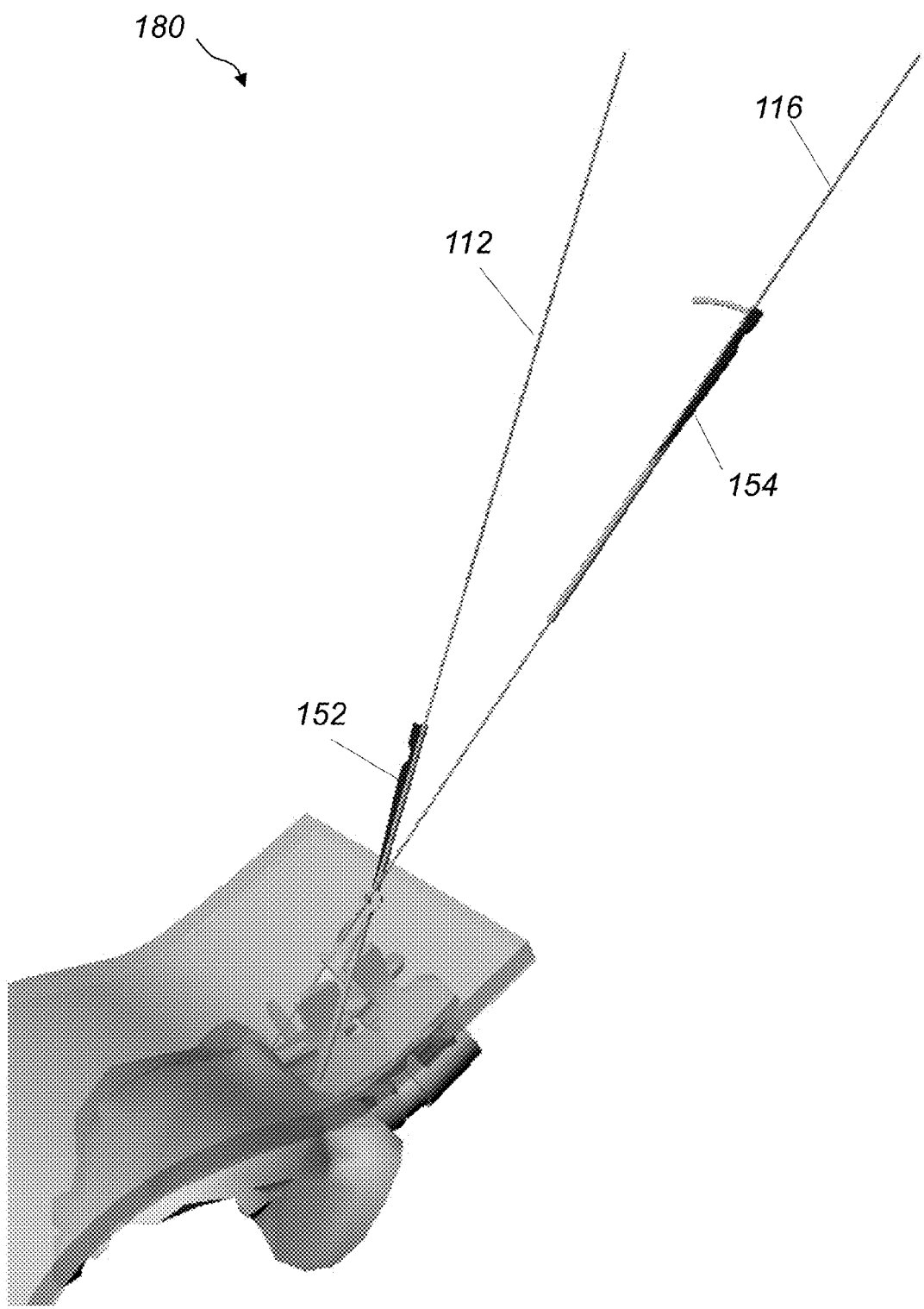
FIG. 9 depicts removing the second guide member.
Figure 10:
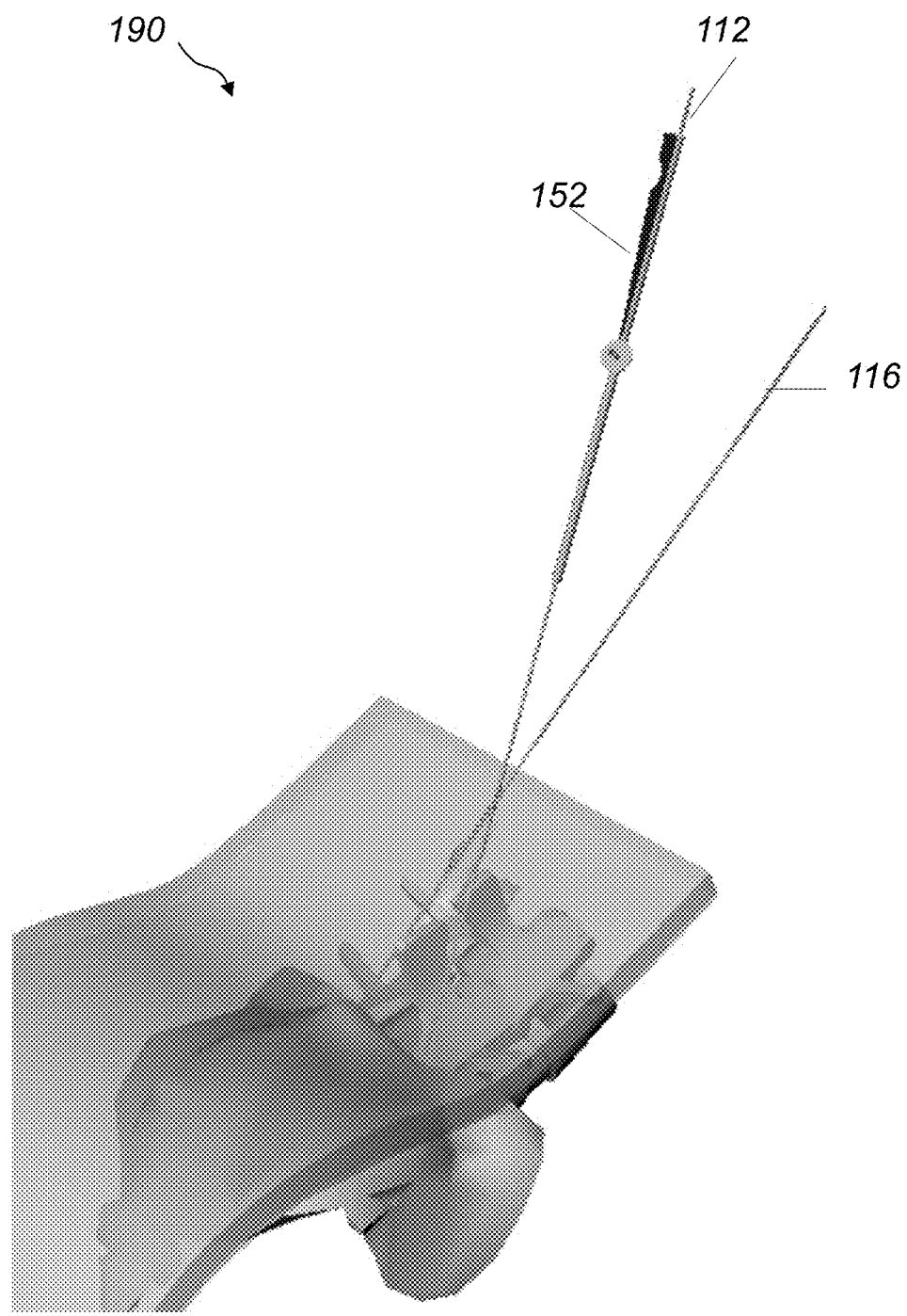
FIG. 10 depicts removing the first guide member.

Referring to FIG. 1-FIG. 19 a new method for facet fixation includes the following steps. First, patient 80 is positioned prone, lying flat on an operating table in preparation for a minimally invasive surgery (MIS) (100). Next, location 114a corresponding to a first facet joint of the L5 lumbar vertebra 84, is radiographically identified and marked on the patient's lower back. For MIS procedures, a skin incision 81 is performed and a first guide wire 112 is inserted in the facet joint location 114a (110). The placement of the guide wire 112 is verified by taking a fluoroscopic image of the patient's back. The fluoroscopic image is further used to identify the location of the facet joints 114a, 114b of vertebra 84 and the angular relationship between them. Guide wire 112 or Kirschner wire (also called K-wire) is a thin, rigid wire that is used to stabilize bone fragments in orthopedics and other types of medical and veterinary surgery. Kirschner wires were introduced in surgical procedures by Martin Kirschner in 1909. They are sterilized, sharpened, smooth stainless steel pins and have different sizes. These wires can be drilled through the bone to hold bone fragments in place. They are placed percutaneously (through the skin), thus avoiding an operation in some cases. In other cases, the K-wires are used after an operation to hold bone fragments in place. In some cases the K-wires include threads for threading into the bone. In spine surgery K-wires are used as guide wires for the placement of spine fixation components, such as screws and pins. They are inserted either through an open surgical procedure or under fluoroscopic or X-ray observation and are removed after the insertion of the screws. In one example guide wire 112 is a threaded 140 millimeter K-wire, manufacture by SpineFrontier, Inc (Beverly, Mass.).

Figure 11:
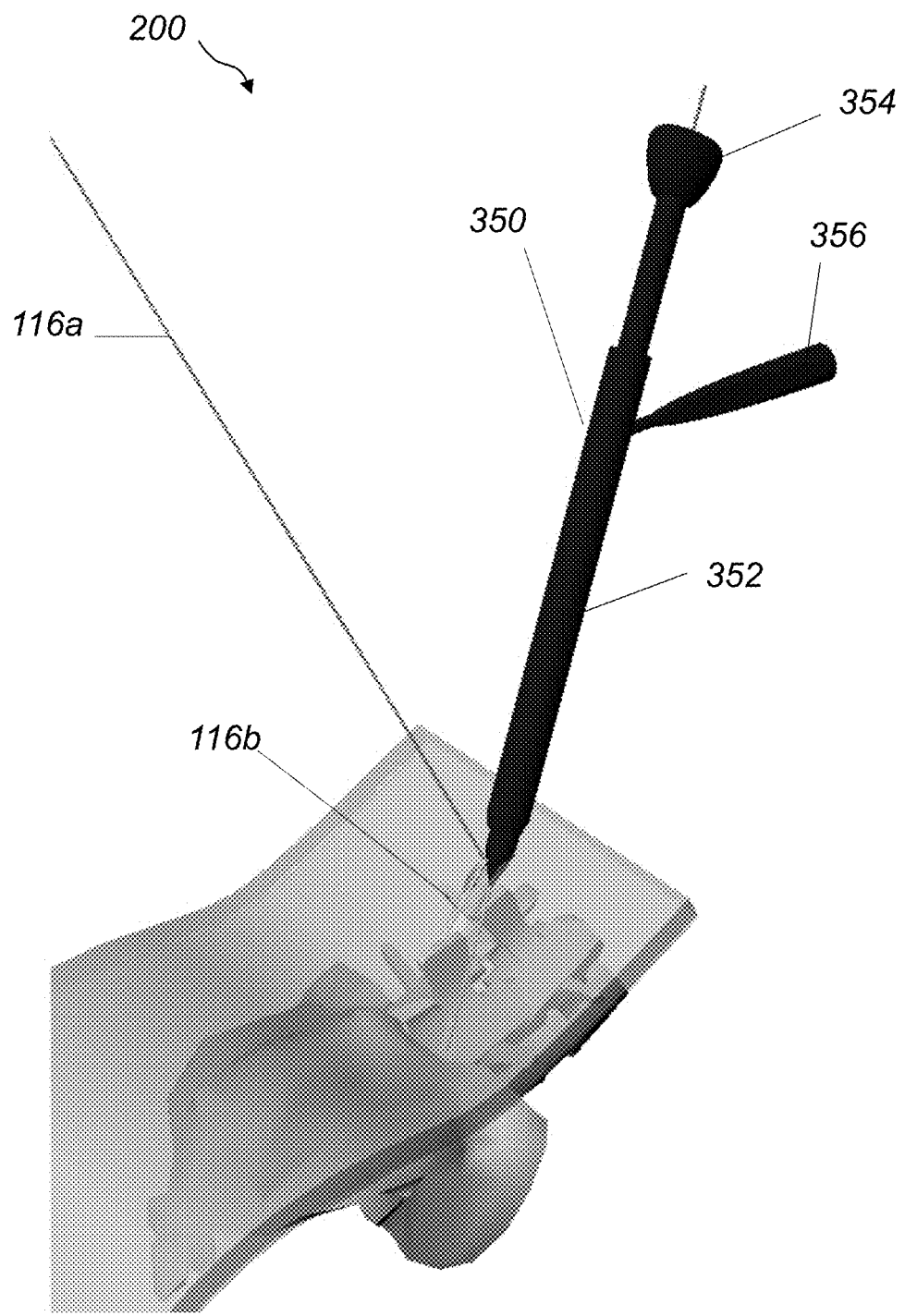
FIG. 11 depicts inserting a tissue dilator into over the first guide wire.
Figure 12:
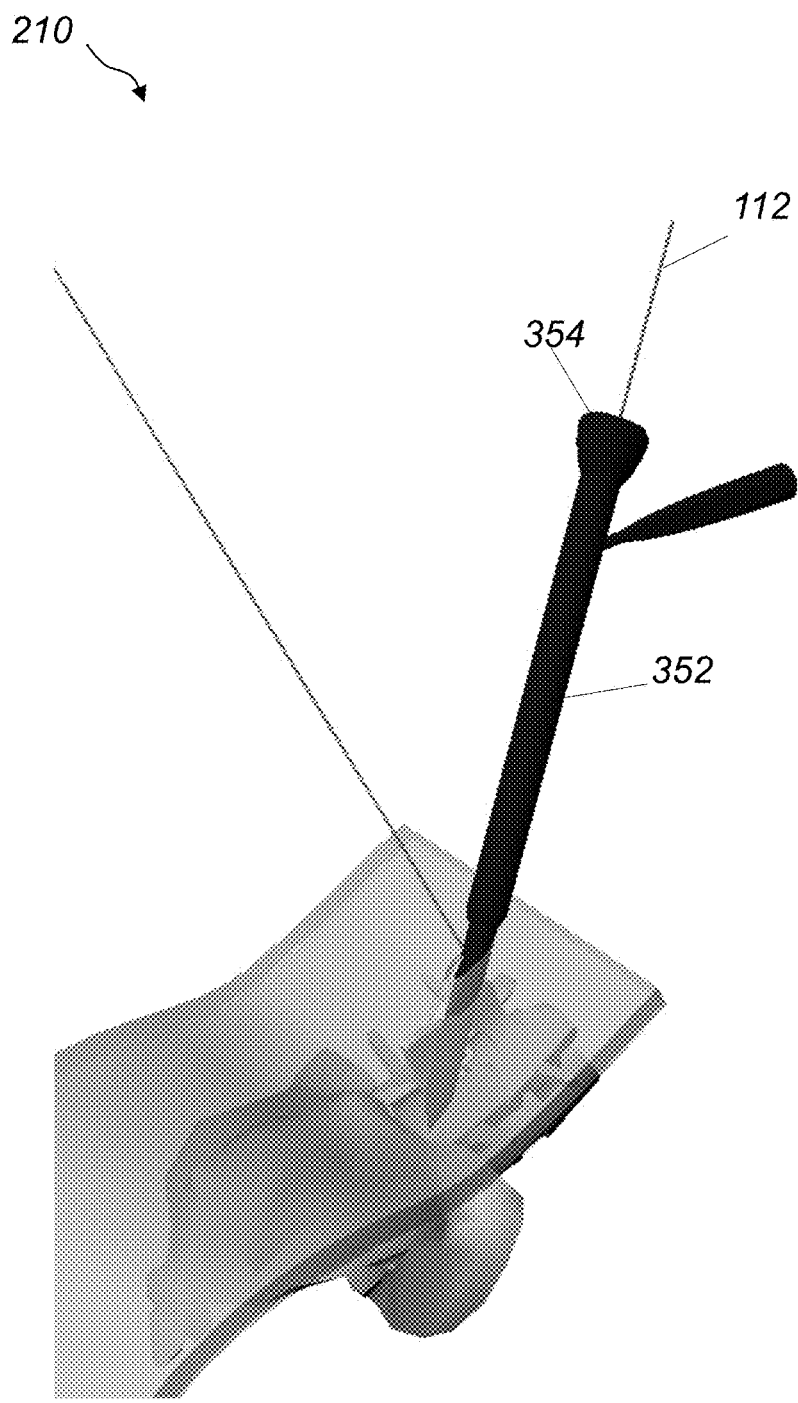
FIG. 12 depicts dilating the tissue around the first guide wire.
Figure 13:
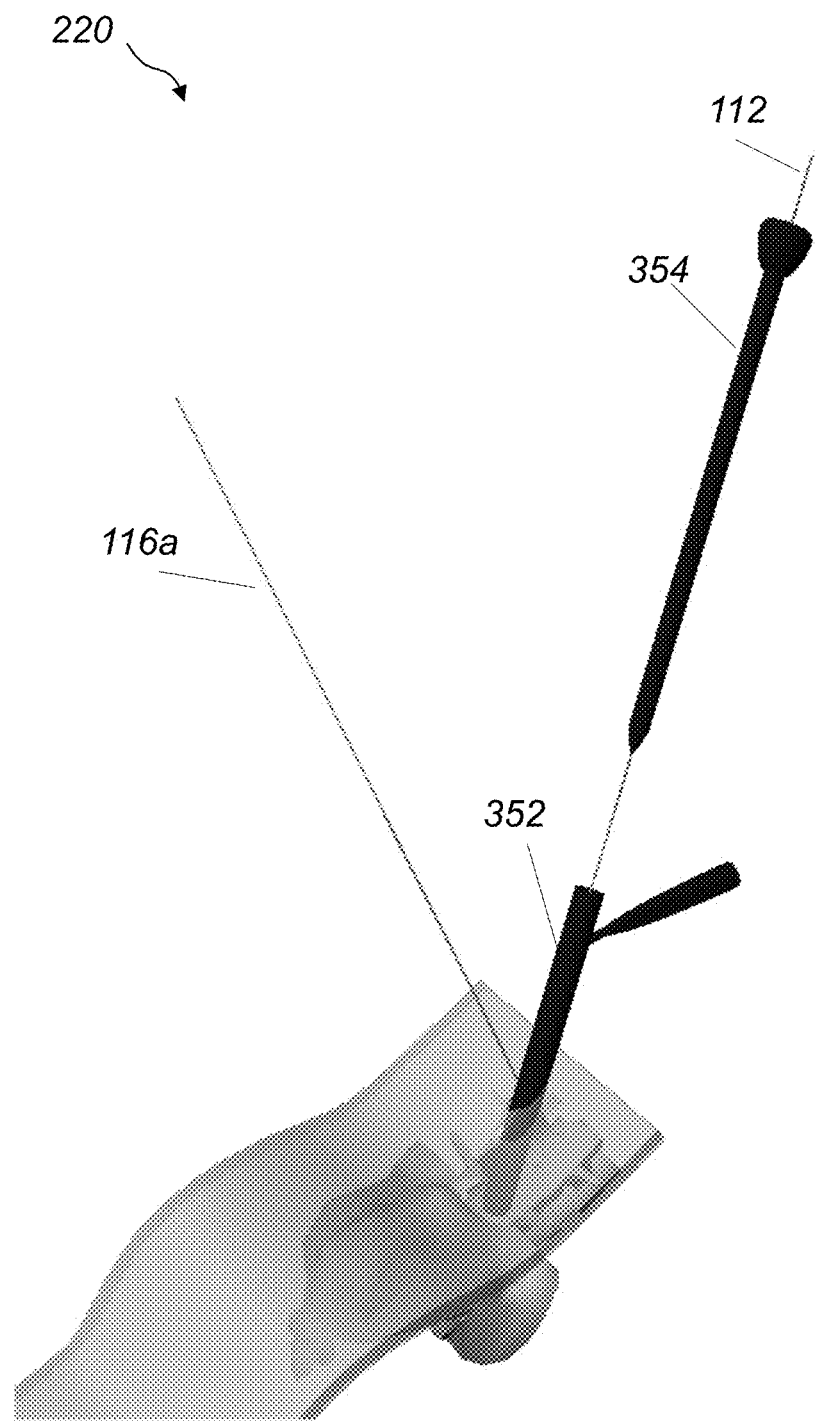
FIG. 13 depicts removing the inner dilator member.
Figure 14:
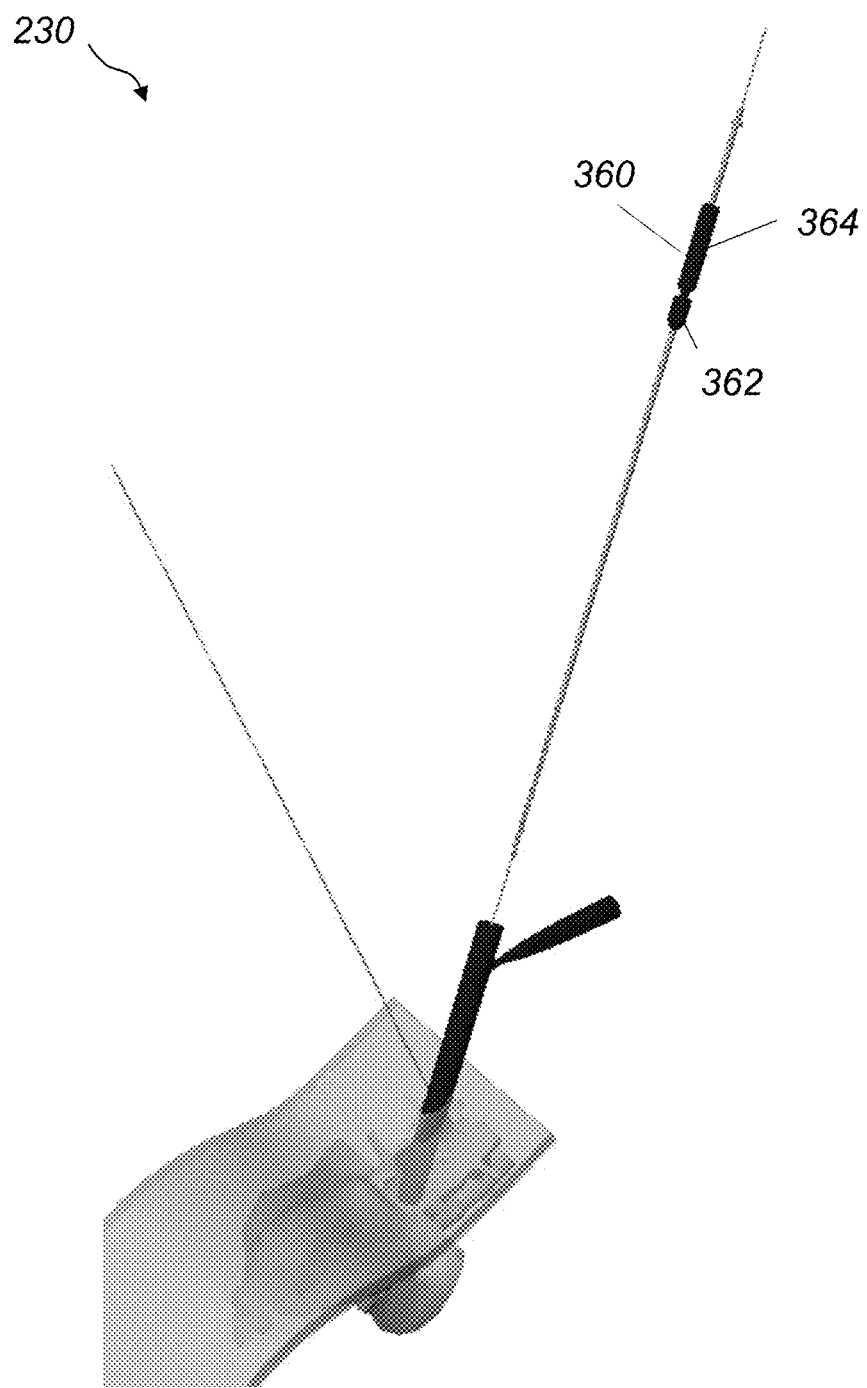
FIG. 14 depicts inserting a drill into the outer dilator member.
Figure 15:
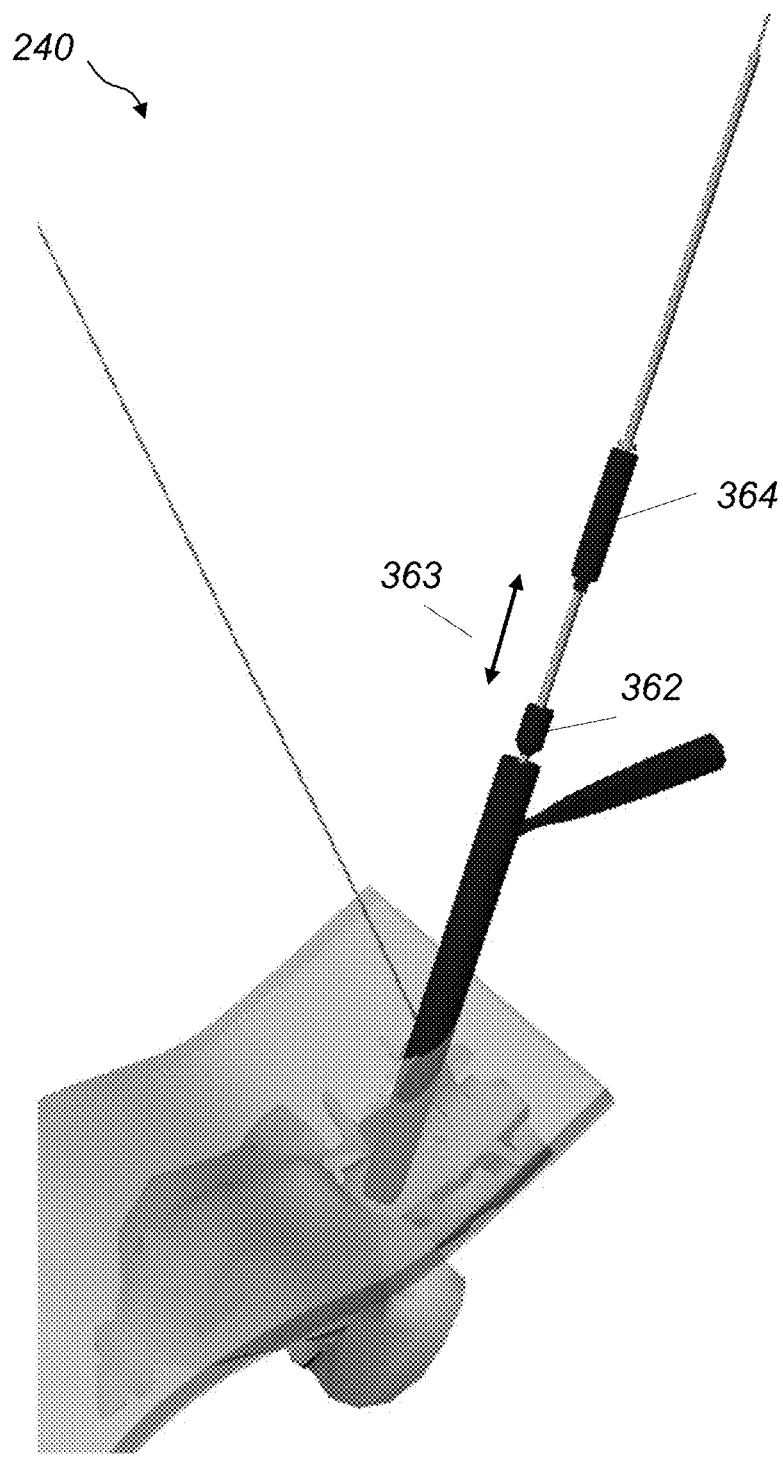
FIG. 15 depicts drilling into the bone around the first guide wire.
Figure 16:
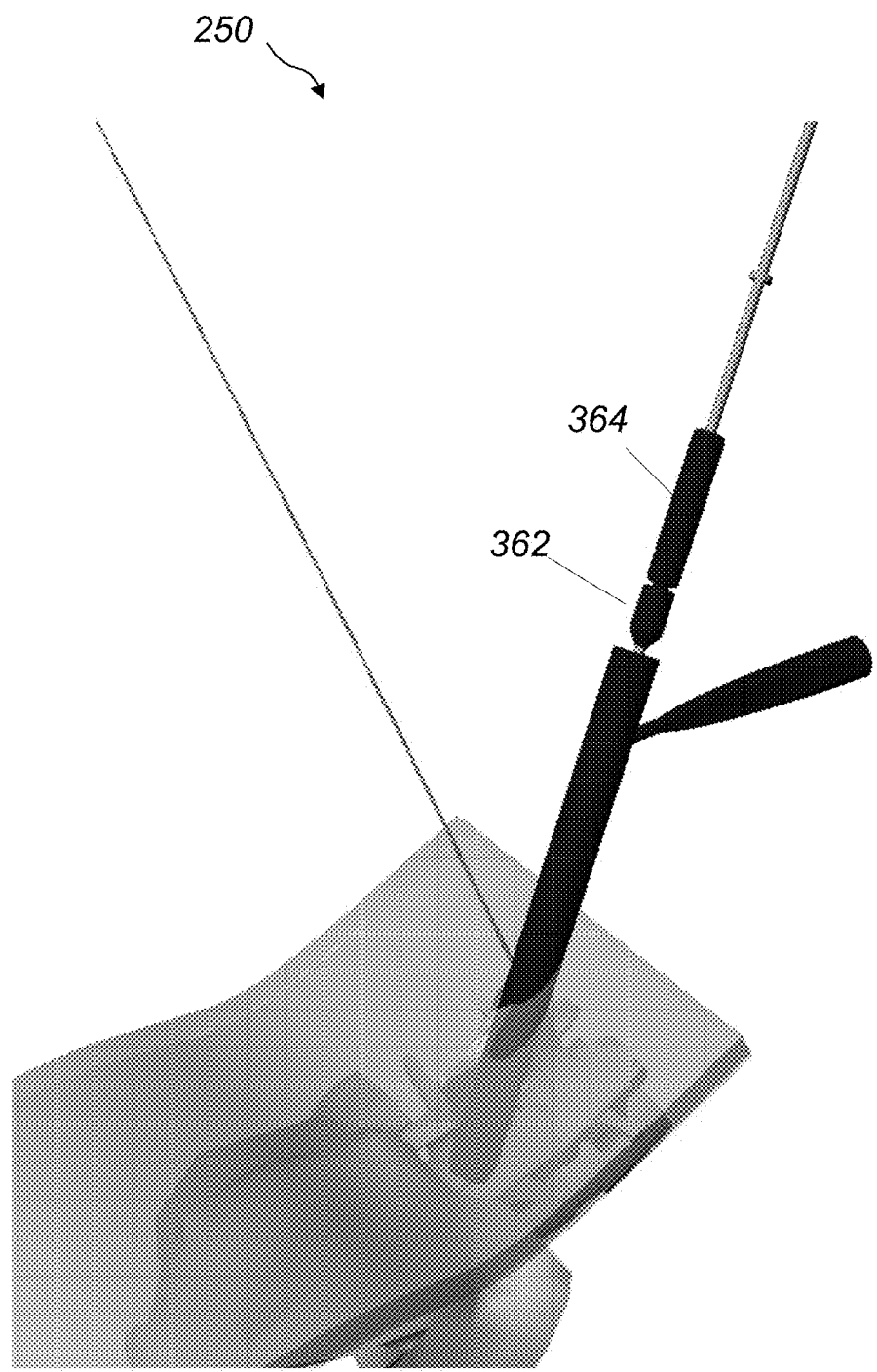
FIG. 16 depicts the automatic stopping mechanism of the drilling process.
Figure 17:
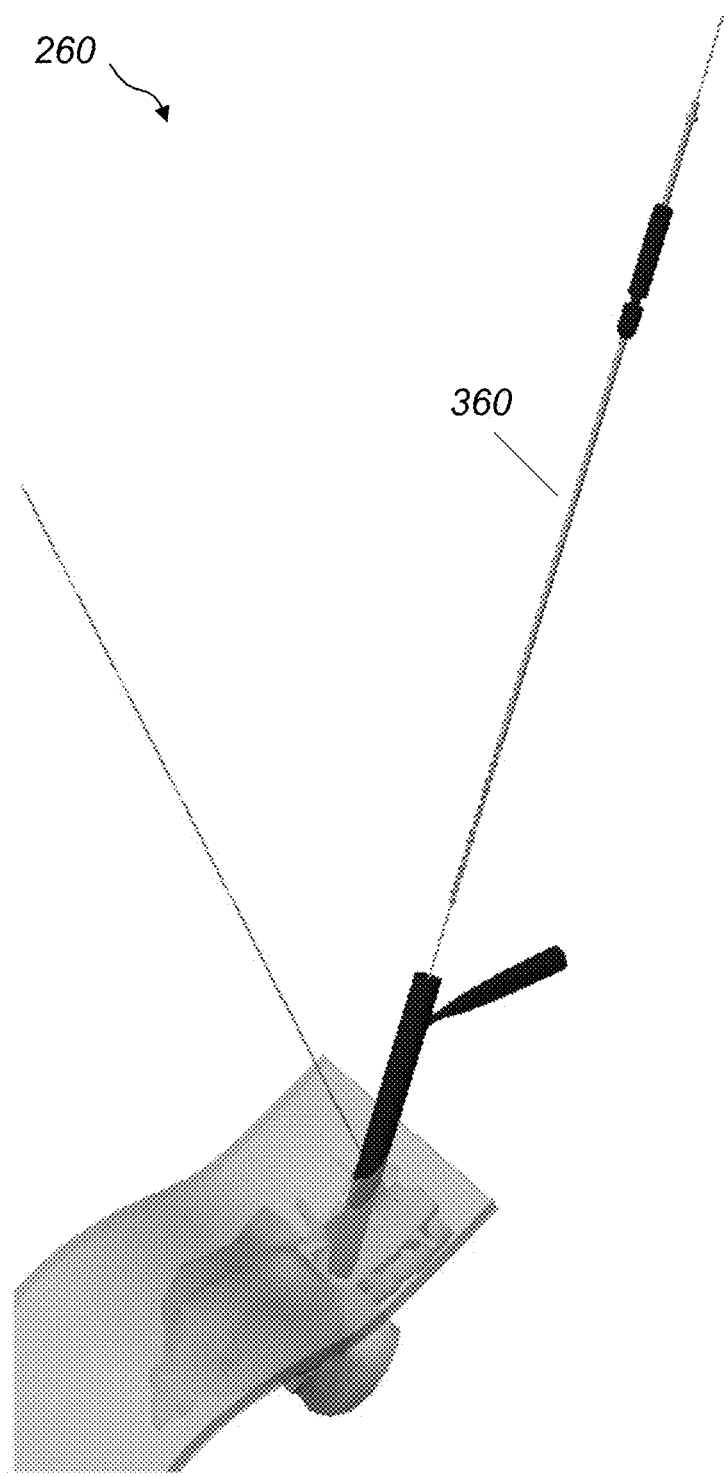
FIG. 17 depicts removing the drill.
Figure 18:
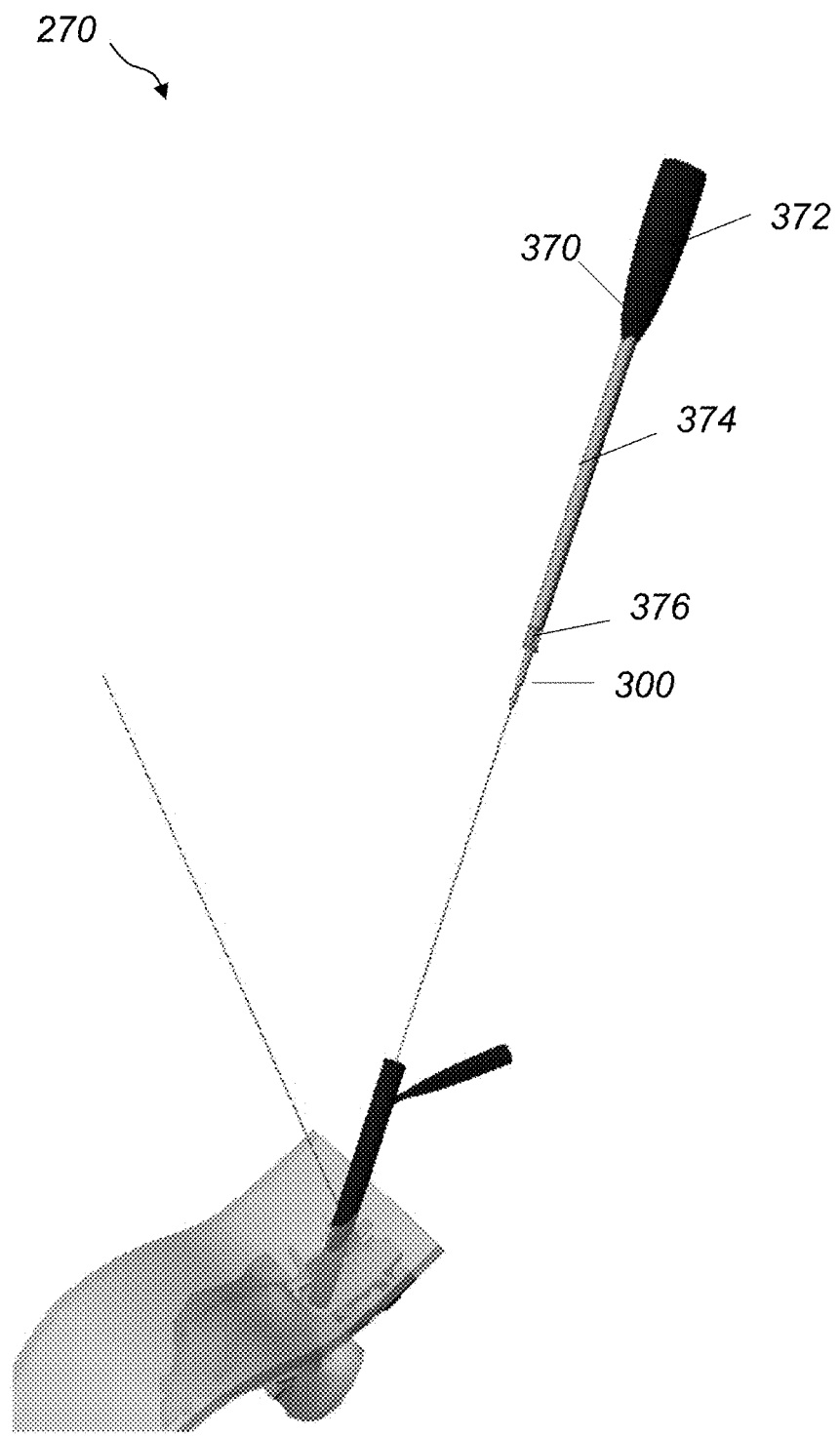
FIG. 18 depicts inserting a first facet screw into the opening over the first guide wire.
Figure 19:
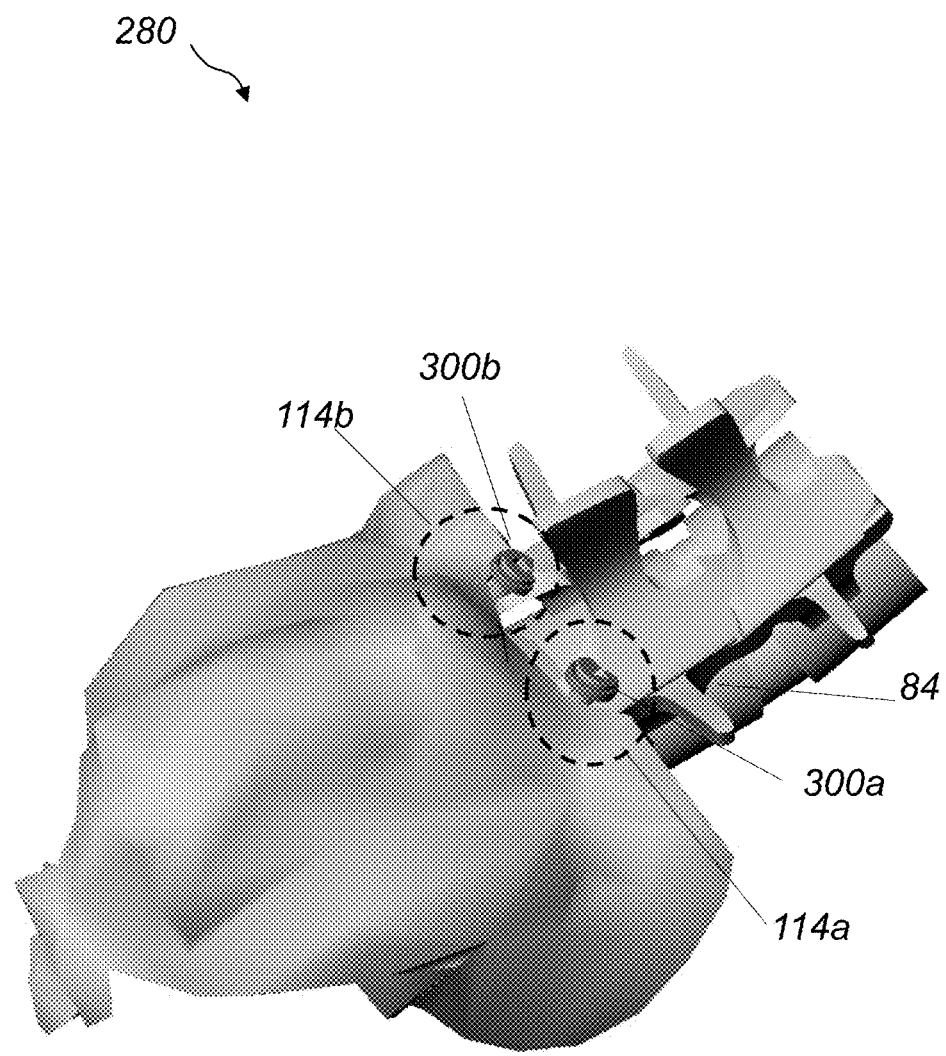
FIG. 19 is a schematic diagram of the lower vertebra with the installed facet screws.
Figure 20:
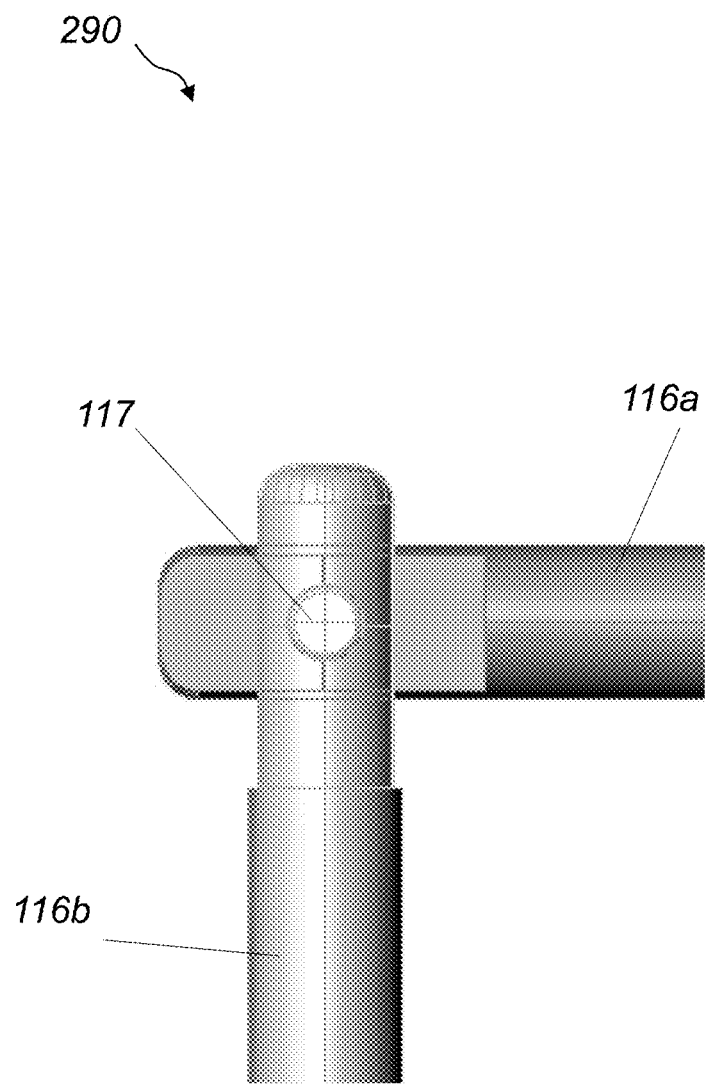
FIG. 20 is a schematic diagram of a pivoting guide wire.
Figure 24:
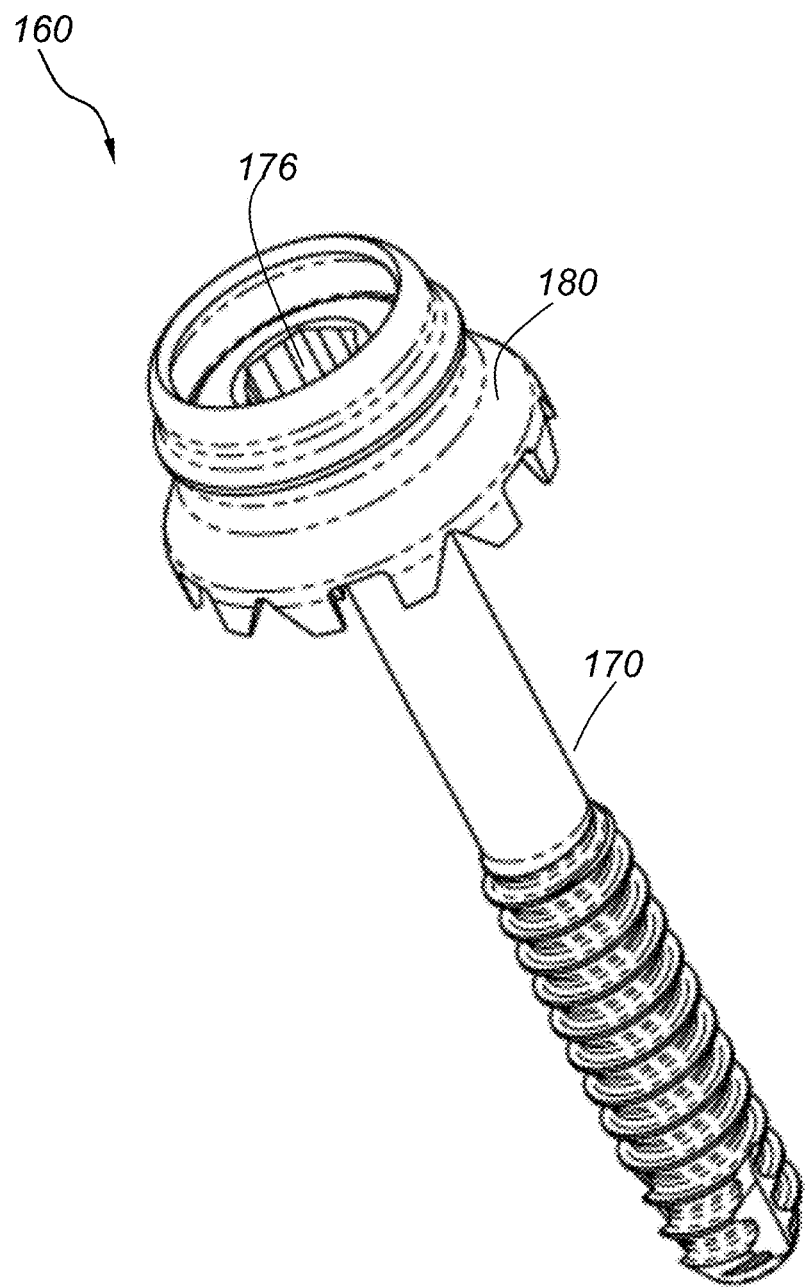
FIG. 24 is a perspective view of another embodiment of the polyaxial facet screw assembly.
Figure 25:
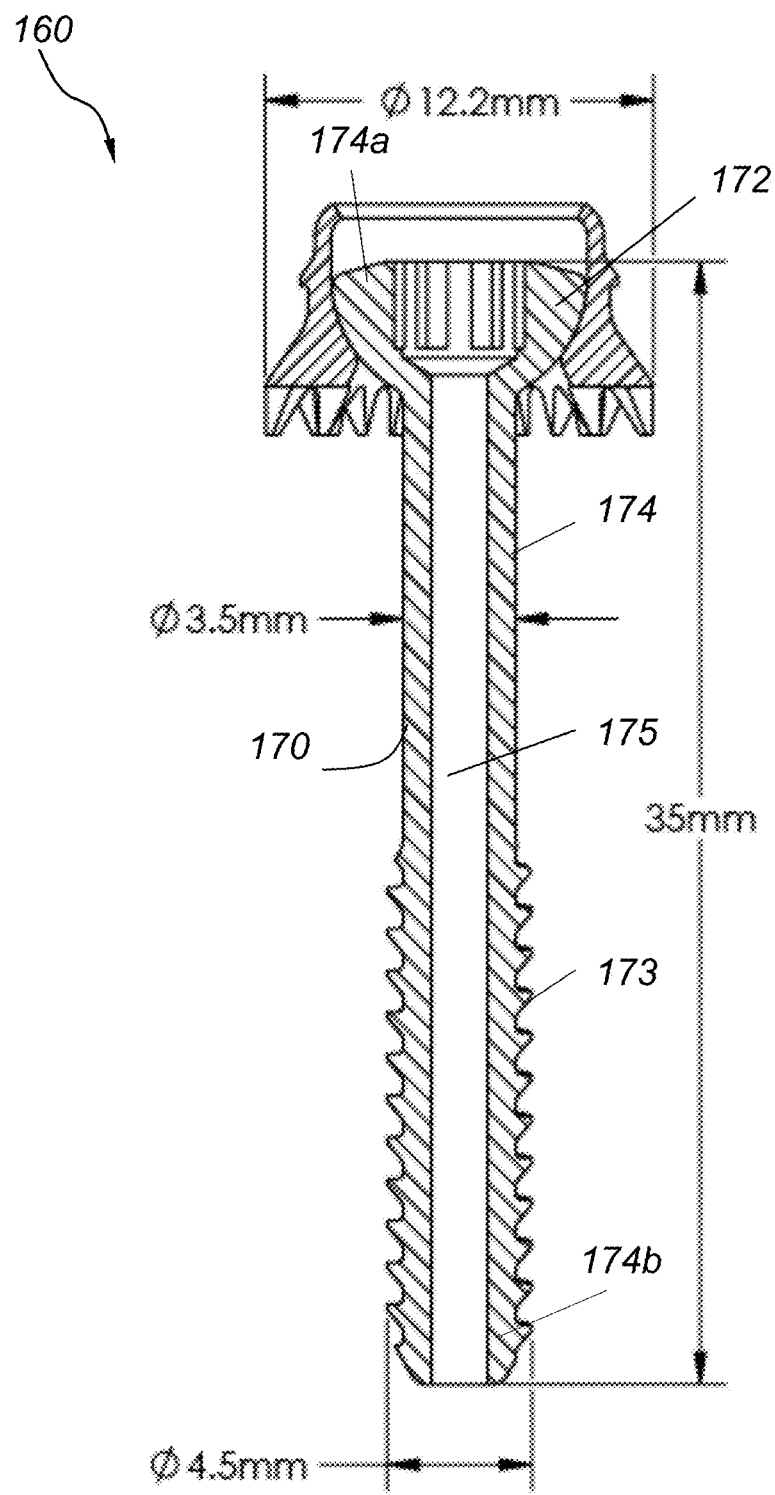
FIG. 25 a cross-sectional side view of the facet screw assembly of FIG. 24.
Figure 26:
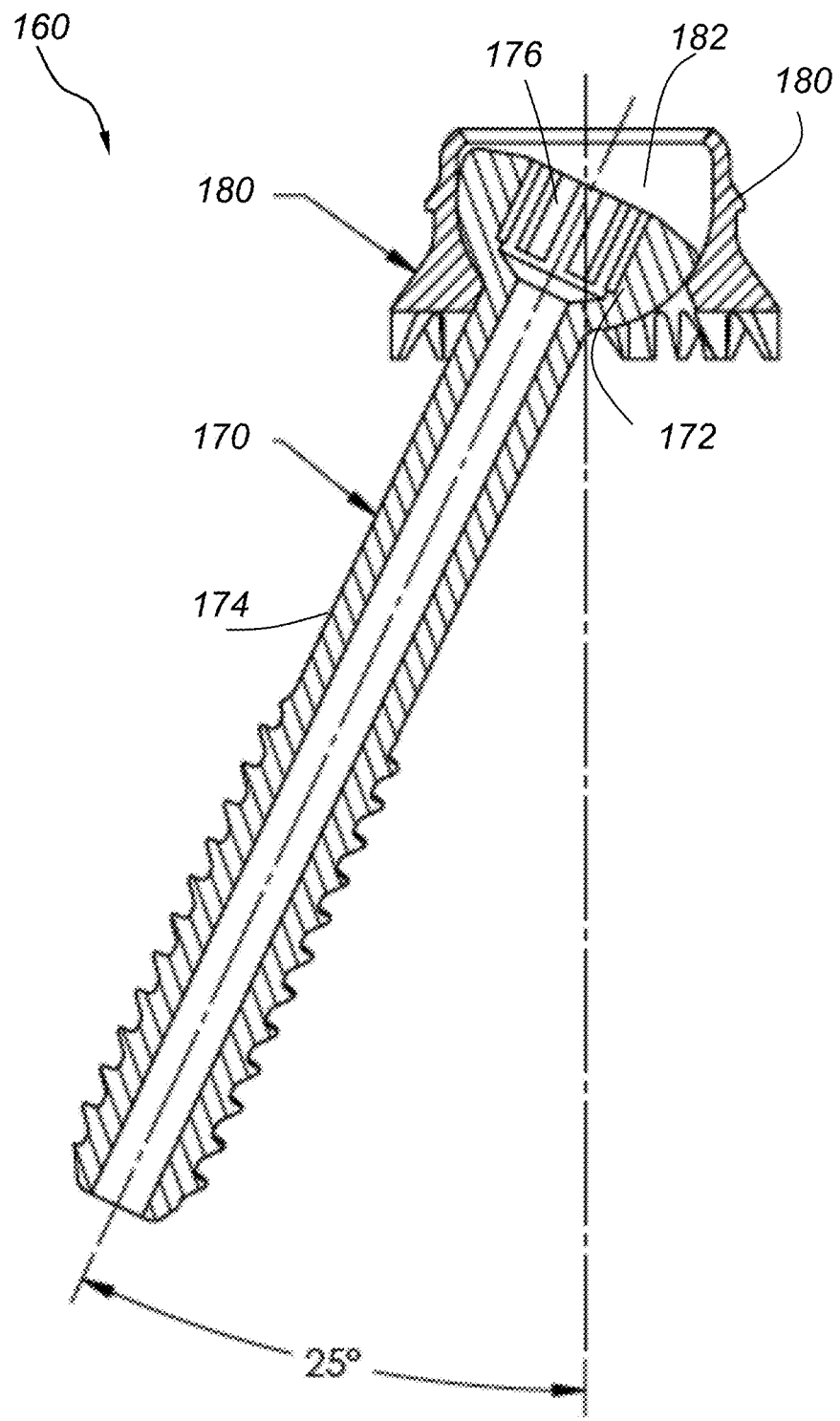
FIG. 26 is another cross-sectional side view of the facet screw assembly of FIG. 24.

Next, a bone needle 122 is inserted over the guide wire 112 (120) and tapped into the facet joint 114a (130). I one example, bone needle 122 is a Jamshide bone needle, manufactured by Baxter-Allegiance. The bone needle is then removed (140), and first arm 152 of an X-guide tool 400 is inserted over the guide wire 112 (150). Second arm 154 of the X-guide tool 400 is connected to the first arm 152 at pivot point 156 (160) and the angle 60 between the two arms 152, 154 is set so that a second guide wire 116 inserted through the second arm will meet the location of the second facet joint 114b of vertebra 84. Angle 60 was determined from the fluoroscopic image of the patient's back, as was mentioned above. Second guide wire is then inserted through the second arm 154 of the X-guide tool 400 into the location of the second facet joint 114b (170). Second guide wire 116 includes two elongated members 116a, 116b pivotally connected at point 117, as shown in FIG. 20. In one example, guide wire 116 is a threaded 50 centimeter pivoting K-wire, manufacture by SpineFrontier, Inc (Beverly, Mass.) and the X-guide tool 400 is a two arm angular positioning guide manufactured also by SpineFrontier, Inc (Beverly, Mass.). Next, the two guide arms 154, 152 are removed (180), (190), and the upper arm 116a of the pivoting guide wire 116 is pivoted out of the plane of the first guide wire 112, as shown in FIG. 11 (200). A tissue dilator 350 is then inserted over the first guide wire 112 (200). Tissue dilator 350 include an outer dilator cannula 352 and an inner dilator 354 configured to slide within the outer dilator cannula 352, as shown in FIG. 24. In one example, tissue dilator 350 is a dilator manufactured by SpineFrontier, Inc (Beverly, Mass.). The inner dilator 354 is advanced within the outer dilator cannula and the tissue around the first guide wire 112 is dilated (210). Next the inner dilator 354 is removed and the outer dilator cannula 352 is advanced into the patient's tissue (220), as shown in FIG. 13. Next a hand drill 360 is inserted into the outer dilator cannula (230). Referring to FIG. 25, hand drill 360 has a handle 364 and an adjustable stop 362. The distance 363 between the drill stop 362 and handle 364 is adjusted to correspond to the length of the facet screw that need to be inserted into the facet joint 114a. Accordingly, in step 240 length 363 is adjusted to match the length 301 of the facet screw 21, shown in FIG. 21 and then the handle is advanced down until it hits the stop 362 (250). In one example, hand drill 360 is a drill manufactured by SpineFrontier, Inc (Beverly, Mass.). Next, the hand drill 360 is removed (260) and a screwdriver 370 with a removable attached screw 300 is inserted in the location 114a via the outer dilator cannula 354 (270). The screw 300 is attached to location 114a and the screwdriver 370 and the outer dilator cannula 354 are removed. Referring to FIG. 26, in one example screwdriver 370 has a removable screw attaching mechanism 376 and is manufactured by SpineFrontier, Inc (Beverly, Mass.).

Next, the upper arm 116a of the second guide wire 116 is straighten and the process of dilation, drilling and screw driving is repeated for the second facet joint location 114b resulting in two facet joint screws 300a, 300b being attached to locations 114, 114b, respectively (280). Similarly, additional facet screws are driven in other facet joint locations of adjacent vertebras 82 and 86.

Figure 21:
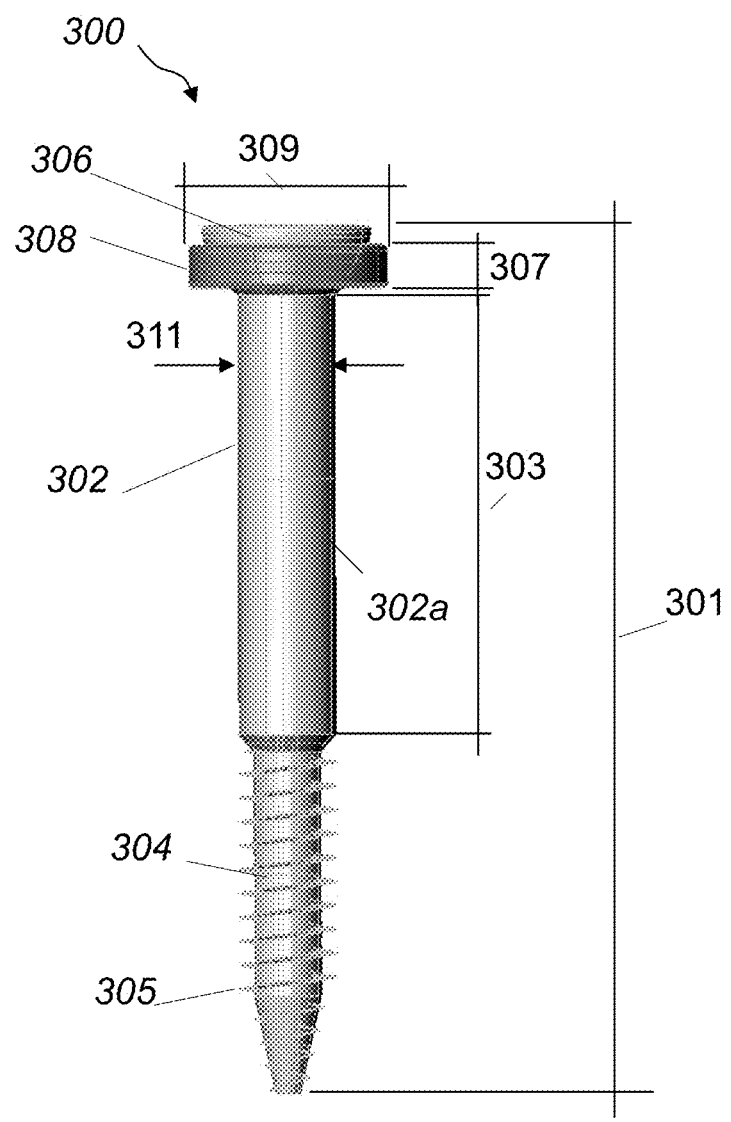
FIG. 21 is a side perspective view of a facet screw assembly.
Figure 22:
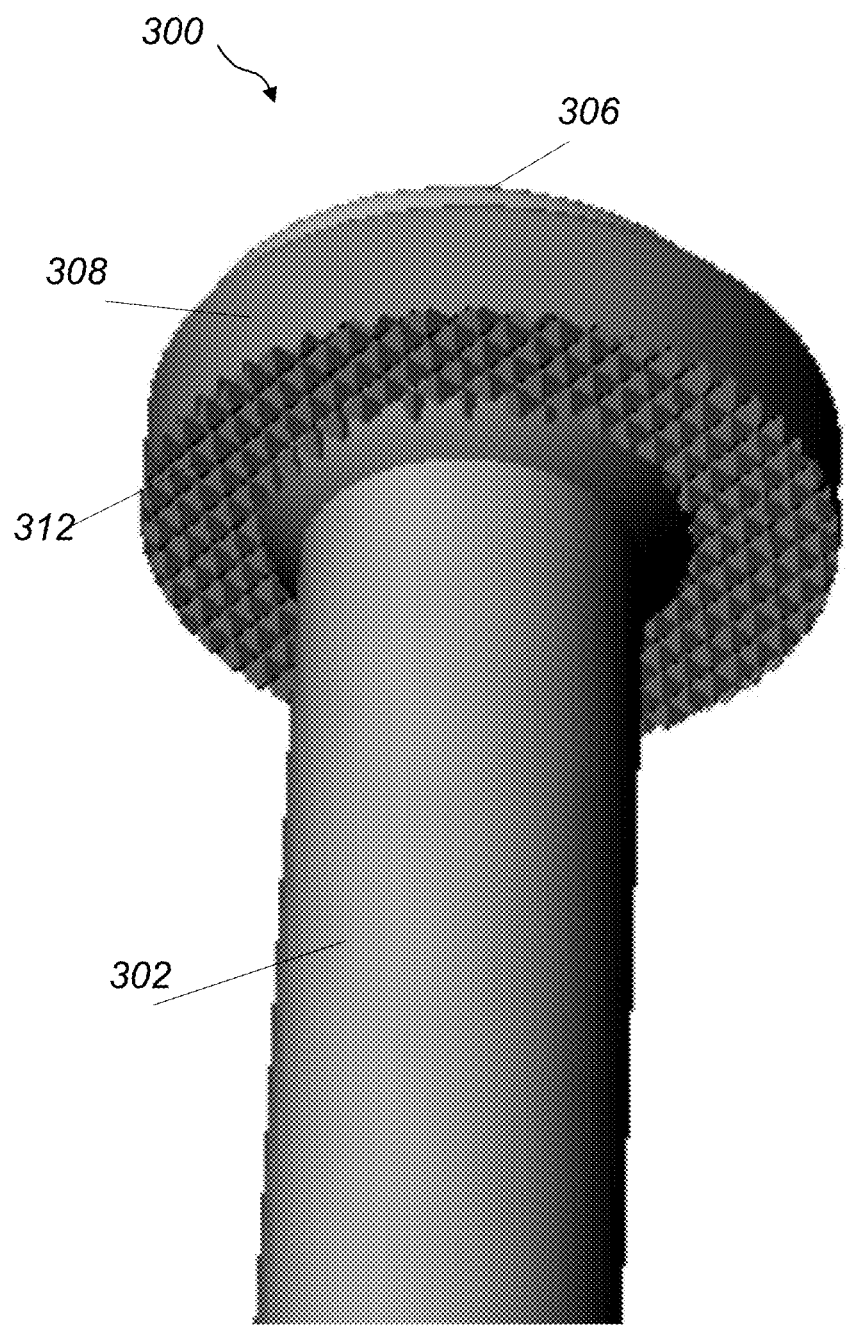
FIG. 22 is a detailed view of the bottom surface of the facet screw washer of FIG. 21.
Figure 23:
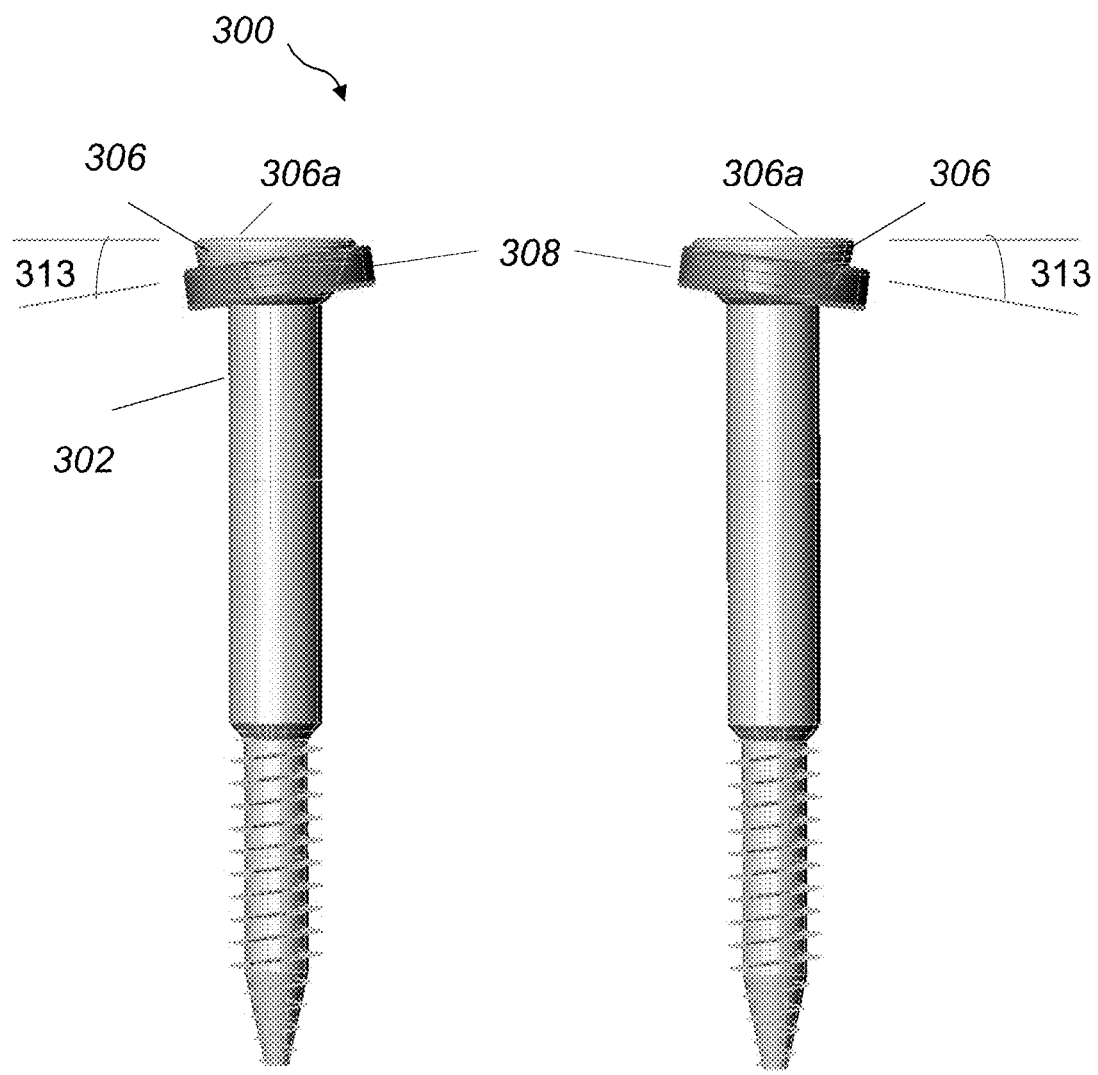
FIG. 23 is a side view of two different orientations of the facet screw washer of FIG. 22.

Referring to FIG. 21, FIG. 22 and FIG. 23, facet screw assembly 300 includes a polyaxial screw 302 and a washer 308. Screw 302 has an elongated body 302a having a semispherical head 306 with a flat top 306a at one end and a threaded portion 304 at the opposite end. Washer 308 is non-removably fitted around head 306. Washer 308 has a semispherical through opening 308a supporting the semispherical head 306 and is configured to pivot around the head 306 at an angle 313, as shown in FIG. 23. Washer 308 also has teeth 312 in its bottom surface for grabbing and holding into the bone, tissue, biologic or synthetic material, as shown in FIG. 22. In other embodiments, the bottom surface of washer 308 include ridges, serrations, grooves, or spikes. In one example, facet screw 300 has a length 301 of about 40 millimeters, a non-threaded portion length 303 of 20 millimeters, screw body width 311 of 4.5 millimeters, washer width 309 of about 9 millimeters, washer height of 2 millimeters and a washer pivoting angle 313 of 7.5 degrees. Facet screw 300 is manufactured by SpineFrontier, Inc (Beverly, Mass.) and may be made of metal such as stainless steel or titanium, plastic, bioabsorbable material, ceramic material, or other solid or porous materials.

Referring to FIG. 24, in another embodiment the facet screw assembly 160 includes a polyaxial screw 170 and a washer 180. Screw 170 has a cannulated elongated body 174 having a through opening 175 extending from its proximal end 174a to its distal end 174b. The elongated body 174 has a semispherical head 172 at the proximal end 174a and a threaded portion 173 at the distal end 174b. The semispherical head 172 is swaged locked within the opening 182 of the washer 180, as shown in FIG. 25. In one example, screw 170 has a length of 35 mm, a diameter of 3.5 mm at the unthreaded body portion and a diameter of 4.5 mm at the threaded body portion. Screw head 172 is polyaxially rotatable within the opening 182 of the washer 180, as shown in FIG. 26, until it is secured into the bone with the screwdriver. The head 172 has a hexagonal through opening 176 for receiving a hexagonal screwdriver tip.

Figure 27:
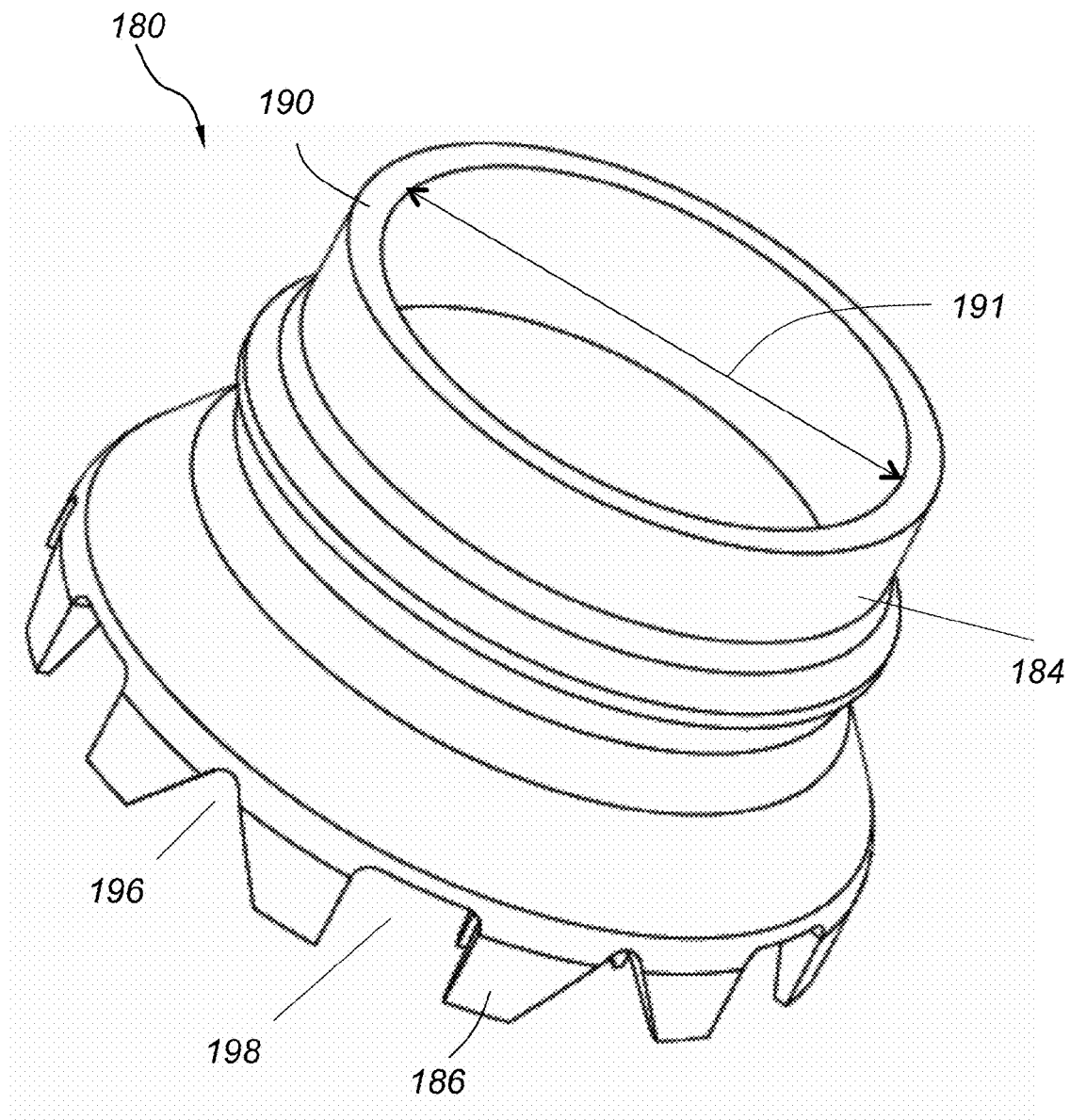
FIG. 27 is a perspective view of the facet screw washer of FIG. 24 before it is swaged and attached to the facet screw.
Figure 28A:
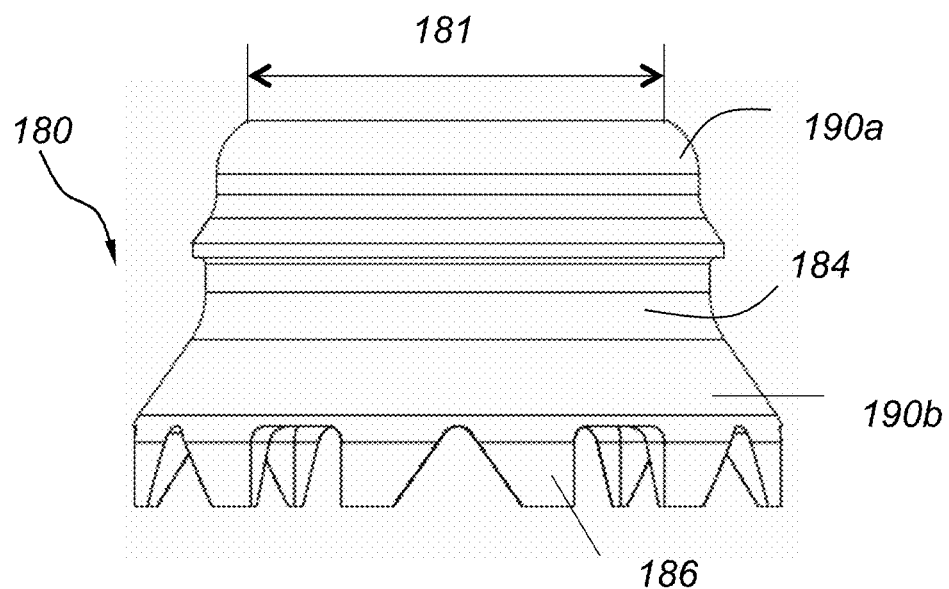
FIG. 28A is a side view of the facet screw washer of FIG. 24 after it is swaged.
Figure 28B:
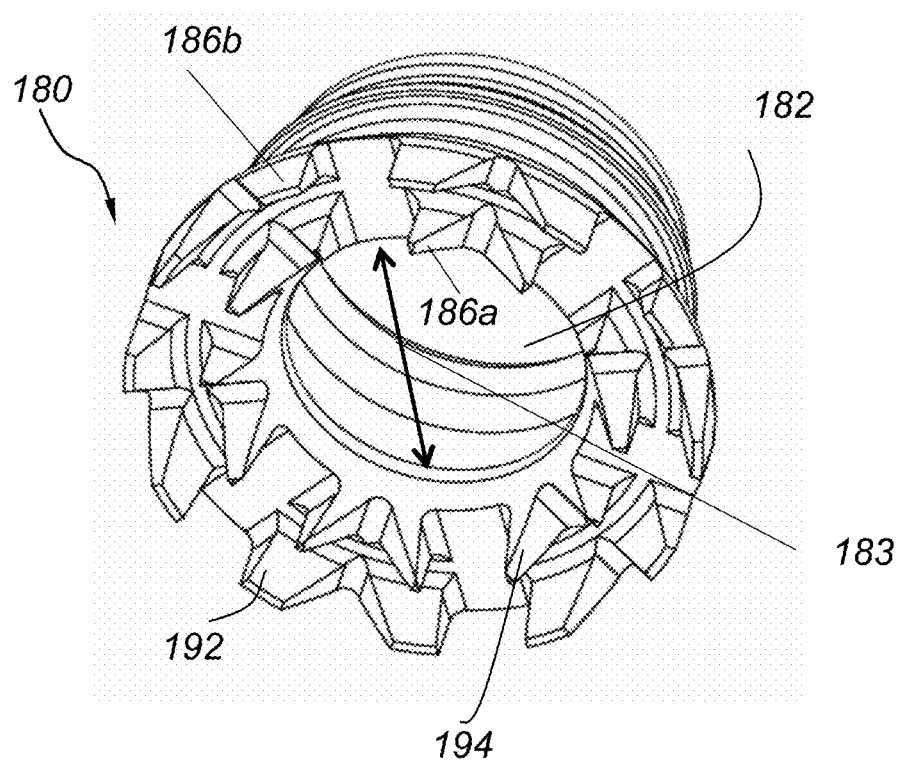
FIG. 28B is a bottom view of the facet screw washer of FIG. 24.

Referring to FIG. 27, FIG. 28A, and FIG. 28B washer 180 has a cylindrical body 184 with a top 190a and a bottom 190b. Two concentric rows (inner 186a, outer 186b) of teeth 186 extend from the bottom 190b of the washer body 184. Cylindrical body 184 has a semispherical through opening 182 for holding the semispherical screw head 172. The opening 182 at the top 190a is initially straight, as shown in FIG. 27, and is flared inwards (i.e., swaged) after the screw head 172 is placed into the opening 182 to lock the head 172 into the opening 182 and prevent it from moving up, as shown in FIG. 28A and FIG. 24. The diameter 191 of the opening 182 at the top 190a is initially slightly larger than the diameter of the semispherical head and becomes slightly smaller 181 after the swaging. The opening 182 at the bottom 190b has a diameter 183 smaller than the diameter of the semispherical head 172 and larger than the diameter of the unthreaded portion of the elongated screw body 174, thus preventing the head 172 from passing through the opening. Inner row 186a has teeth 186 with trigonal cross-section 194 and outer row 186b has teeth with rectangular cross-section 192. The gaps 198, 196 between the teeth 186 in each row have alternating rectangular and trigonal shapes, respectively. This teeth geometry and arrangement allow the washer to penetrate and grab into the bone or tissue and to prevent it from rotating once it is engaged into the bone or tissue. The washer pierces the bone/tissue in order to achieve a more secure padding for compression and distributes the compression force onto a flatter wider surface. The piercing of the bone by the washer also promotes bone growth.

Figure 29:
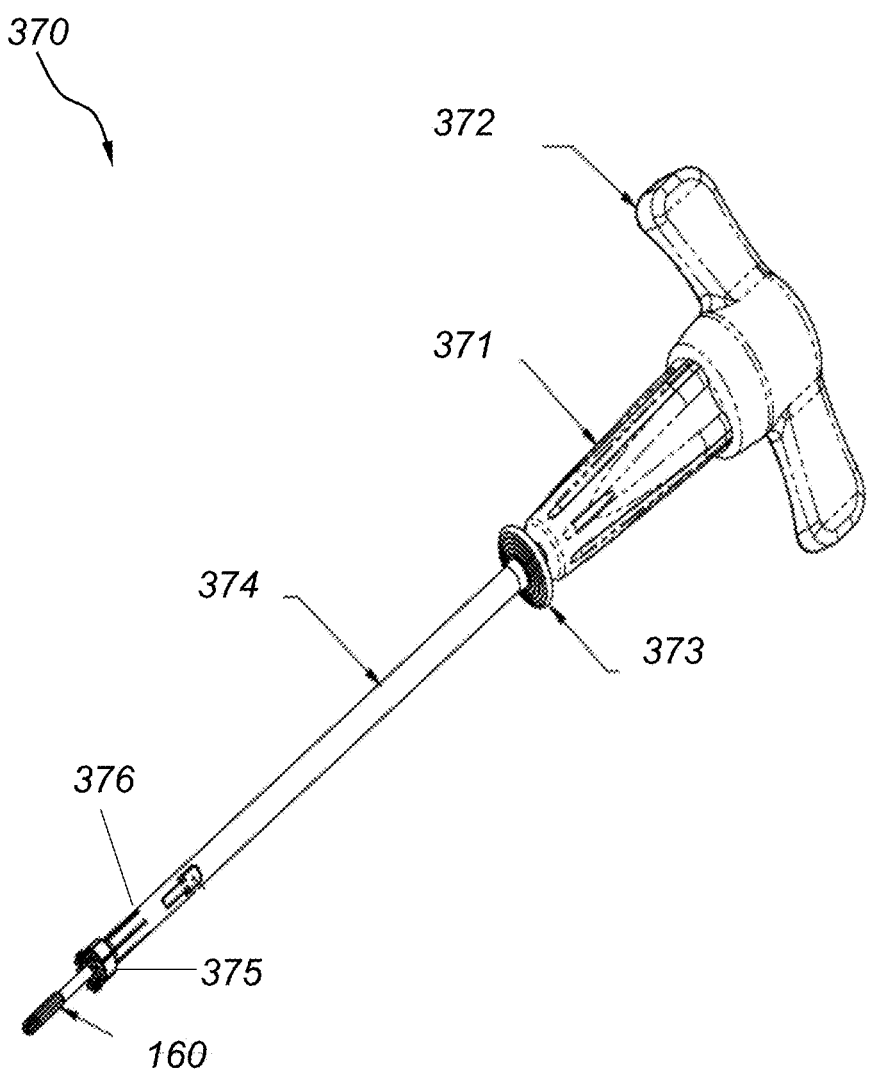
FIG. 29 is a perspective view of a screwdriver assembly.
Figure 30A:
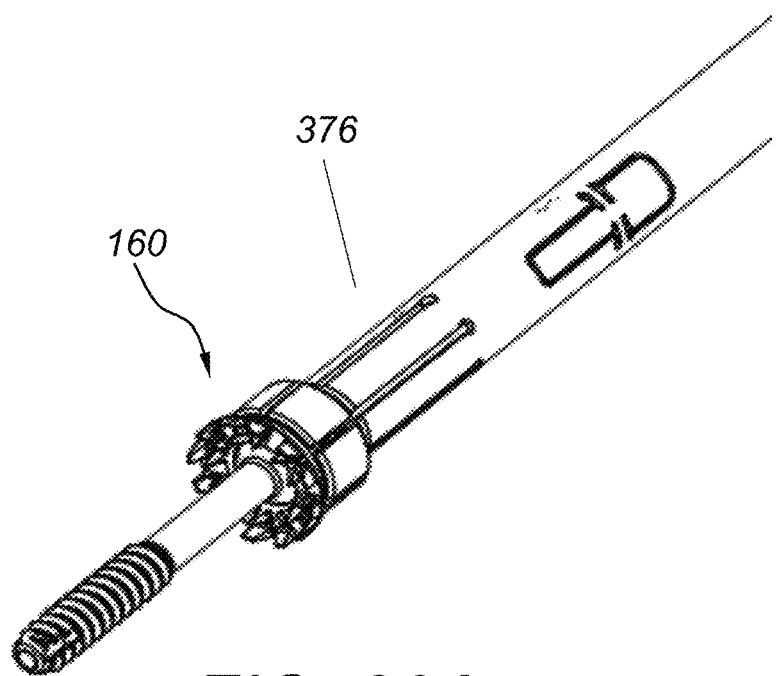
FIG. 30A is a detailed view of the lower portion of the screwdriver assembly of FIG. 29 with the facet screw assembly retained.
Figure 30B:
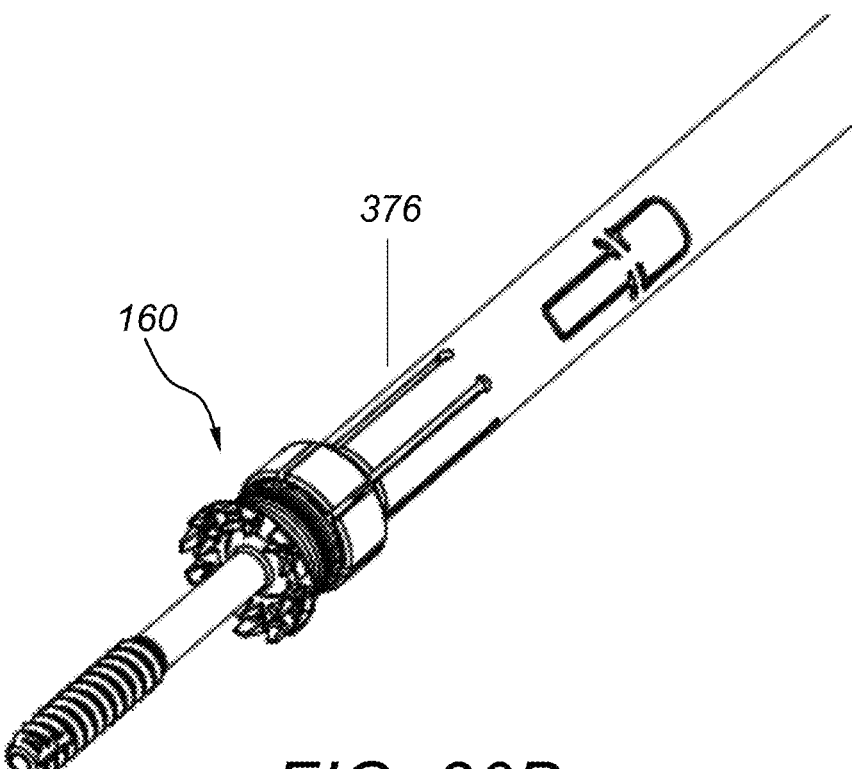
FIG. 30B is a detailed view of the lower portion of the screwdriver assembly of FIG. 29 with the facet screw assembly released.

Referring to FIG. 29, a screwdriver assembly 370 is used to deliver and screw the facet screw assembly 160 into the bone through the cannula 202. The screwdriver assembly 370 includes a screw retention sleeve 374 and a handle 371 attached to the proximal end of the retention sleeve 374. Handle 371 includes a detachable T-shaped component 372 that can be used to provide additional torque for driving the screw assembly 160 into the bone. The screw assembly 160 is attached to the distal end 376 of the retention sleeve 374 and can be released or retained by moving the screw release/capture component 375 up or down. Detailed views of the retained and released facet screw assembly are shown in FIG. 30A, and FIG. 30B, respectively.

Several embodiments of the present invention have been described. Nevertheless, it will be understood that various modifications may be made without departing from the spirit and scope of the invention. Accordingly, other embodiments are within the scope of the following claims.

What is claimed is:

1. A spinal fixation element comprising:
    a polyaxial screw comprising a cannulated elongated cylindrical body of a first diameter, said cannulated elongated cylindrical body comprising a threaded portion at a distal end and a head at the proximal end and wherein said head comprises a flat top and a semispherical bottom of a second diameter, wherein said second diameter is larger than said first diameter; and
    a washer comprising a cylindrical upper portion, a flared out lower portion and a semispherical through opening and wherein said semispherical through opening comprises a third diameter at the top, a fourth diameter in the middle and a fifth diameter at the bottom, and wherein said third diameter is slightly smaller than said second diameter, said fourth diameter is slightly larger than said second diameter and said fifth diameter is smaller than said second diameter, and wherein said washer is configured to receive and hold said head within said semispherical through opening, is non-removably attached to said head by swaging the cylindrical upper portion and is rotatable and positionable at an angle relative to said elongated body.

2. The fixation element of claim 1 wherein said washer comprises two concentric circular rows of protrusions extending from a bottom surface of the lower portion and wherein said protrusions comprise at least one of spikes, teeth, serrations, grooves, or ridges.

3. The fixation element of claim 2 wherein said protrusions are spaced apart by gaps having alternating trigonal and rectangular shapes.

4. The fixation element of claim 3 wherein said protrusions are arranged around an outer circular row and an inner circular row and wherein the protrusions of the outer circular row comprise teeth with rectangular cross-section and the protrusions of the inner circular row comprise teeth with trigonal cross-section.

5. The fixation element of claim 1 wherein said angle varies between +30 degrees and −30 degrees.

6. The fixation element of claim 1 wherein said cannulated elongated body comprises a through opening extending from the proximal end to the distal end.

7. The fixation element of claim 1 wherein said head comprises a through opening being concentric with said through opening of said elongated body.

8. The fixation element of claim 1 comprising one of stainless steel, titanium, plastic, bioabsorbable material, ceramic material, solid or porous material.

9. The fixation element of claim 1 wherein said head comprises a hexagonal through opening for receiving a hexagonal screwdriver tip.

* * * * *